United States Patent
Schmidt et al.

(10) Patent No.: US 8,304,436 B2
(45) Date of Patent: Nov. 6, 2012

(54) PYRAZOLONE DERIVATIVES AS PDE4 INHIBITORS

(75) Inventors: Beate Schmidt, Allensbach (DE); Christian Scheufler, Engen-Neuhausen (DE); Juergen Volz, Radolfzell (DE); Martin Feth, Kelkheim-Hornau (DE); Rolf-Peter Hummel, Radolfzell (DE); Armin Hatzelmann, Constance (DE); Christof Zitt, Constance (DE); Andrea Wohlsen, Neuchatel (CH); Degenhard Marx, Moos (DE); Hans-Peter Kley, Allensbach (DE); Deborah Ockert, Hamburg (DE); Anke Heuser, Hamburg (DE); Johannes A. M. Christiaans, DG Lelystad (NL); Geert Jan Sterk, JJ Utrecht (NL); Wiro M. P. B. Menge, HM Arnhem (NL)

(73) Assignee: Nycomed GmbH, Constance (DE)

( * ) Notice: Subject to any disclaimer, the term of this patent is extended or adjusted under 35 U.S.C. 154(b) by 402 days.

(21) Appl. No.: 12/451,348

(22) PCT Filed: May 14, 2008

(86) PCT No.: PCT/EP2008/055867
§ 371 (c)(1),
(2), (4) Date: Nov. 9, 2009

(87) PCT Pub. No.: WO2008/138939
PCT Pub. Date: Nov. 20, 2008

(65) Prior Publication Data
US 2010/0120757 A1      May 13, 2010

(30) Foreign Application Priority Data
May 16, 2007   (EP) .................... 07108314

(51) Int. Cl.
| *A01N 43/40* | (2006.01) |
| *A61K 31/445* | (2006.01) |
| *C07D 401/00* | (2006.01) |
| *C07D 231/00* | (2006.01) |
| *C07D 403/00* | (2006.01) |
| *C07D 403/02* | (2006.01) |

(52) U.S. Cl. ............... 514/326; 546/211; 548/364.1
(58) Field of Classification Search .......... 546/211; 514/326; 548/364.1
See application file for complete search history.

(56) References Cited

U.S. PATENT DOCUMENTS

| 2,903,460 A | 9/1959 | Jucker et al. |
| 6,103,718 A | 8/2000 | Sterk |
| 6,953,853 B2 | 10/2005 | Grundler et al. |
| 7,179,810 B2 | 2/2007 | Grundler et al. |
| 7,186,870 B2 | 3/2007 | Singer et al. |
| 7,220,746 B2 | 5/2007 | Sterk |
| 7,494,990 B2 | 2/2009 | Menge et al. |
| 7,531,540 B2 | 5/2009 | Grundler et al. |
| 2006/0094710 A1 | 5/2006 | Sterk |
| 2006/0167001 A1 | 7/2006 | Sterk |
| 2009/0131448 A1 | 5/2009 | Menge et al. |

FOREIGN PATENT DOCUMENTS

| EP | 0 126 651 A2 | 11/1984 |
| WO | 98/31674 A1 | 7/1998 |
| WO | 02/064584 A1 | 8/2002 |
| WO | 02/085906 A2 | 10/2002 |
| WO | 2004/017974 A1 | 3/2004 |
| WO | 2004/018449 A1 | 3/2004 |
| WO | 2004/018451 A1 | 3/2004 |
| WO | 2004/018457 A1 | 3/2004 |
| WO | 2005/075456 A1 | 8/2005 |
| WO | 2005/075457 A1 | 8/2005 |

OTHER PUBLICATIONS

Norman, Expert Opinion on Therapeutic Patents, 1998, Ashley Publications, vol. 8, issue 7, pp. 771-784.*
Giembycz, Drugs, 2000, Adis International, vol. 59, issue 2, pp. 193-212.*

* cited by examiner

*Primary Examiner* — Sreeni Padmanabhan
*Assistant Examiner* — Sarah Pihonak
(74) *Attorney, Agent, or Firm* — Nath, Goldberg & Meyer; Sheldon M. McGee

(57) ABSTRACT

The compounds of a certain formula 1,

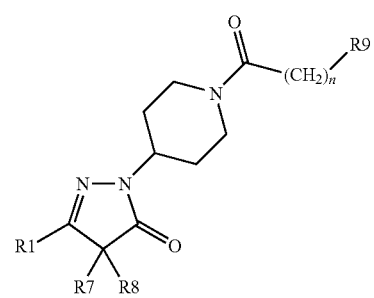

in which R1, R7, R8, R9 and n have the meanings as given in the description, are novel effective inhibitors of the type 4 phosphodiesterase.

13 Claims, No Drawings

PYRAZOLONE DERIVATIVES AS PDE4 INHIBITORS

This application is filed under 35 U.S.C. 371 as the national stage of PCT/EP2008/055867, filed May 14, 2008, which claims priority to EP 07108314.1, filed May 16, 2007.

FIELD OF APPLICATION OF THE INVENTION

The invention relates to novel pyrazolone-derivatives, which are used in the pharmaceutical industry for the manufacture of pharmaceutical compositions.

KNOWN TECHNICAL BACKGROUND

In the International patent application WO98/31674 phthalazinone derivatives are described as PDE4 inhibitors. In the International patent applications WO02/064584, WO02/085906, WO2004/017974, WO2004/018449, WO2004/018451, WO2004/018457, WO2005/075456 and WO2005/075457 phthalazinone- or pyridazinone-derivatives with a piperidinyl substituent are described as PDE4 inhibitors. In the European patent application EP0126651 2,4-dihydro-5-[(substituted) phenyl]-4,4-disubstituted-3H-pyrazol-3-ones and 2,4-dihydro-5-[(substituted) phenyl]-4,4-disubstituted-3H-pyrazol-3-thiones are disclosed for use as cardiotonic and antihypertensive agents. In U.S. Pat. No. 2,903,460 pyrazolone derivatives with a piperidinyl substituent are described as analgetic and antipyretic compounds.

DESCRIPTION OF THE INVENTION

It has now been found that the pyrazolone-derivatives, which are described in greater details below, have surprising and particularly advantageous properties.

The invention relates to a compound of formula 1

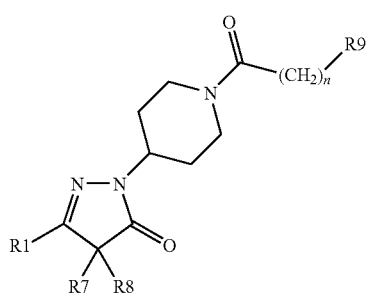

wherein
R1 represents a phenyl derivative of formulae (a) or (b)

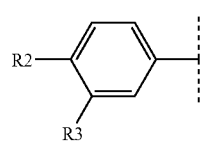

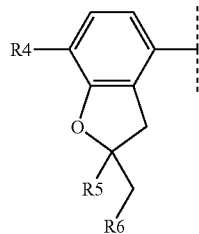

wherein
R2 is selected from the group consisting of 1-2C-alkoxy and 1-2C-alkoxy which is completely or predominantly substituted by fluorine;
R3 is selected from the group consisting of 1-2C-alkoxy, 3-5C-cycloalkoxy, 3-5C-cycloalkylmethoxy and 1-2C-alkoxy which is completely or predominantly substituted by fluorine;
R4 is selected from the group consisting of 1-2C-alkoxy and 1-2C-alkoxy which is completely or predominantly substituted by fluorine;
R5 is 1-2C-alkyl and
R6 is selected from the group consisting of hydrogen and 1-2C-alkyl;
or R5 and R6 together and with inclusion of the two carbon atoms, to which they are bonded, form a spiro-linked 5- or 6-membered hydrocarbon ring;
R7 is 1-3C-alkyl and
R8 is 1-3C-alkyl
or R7 and R8 together with the carbon atom, to which they are bonded, form a spiro-linked 3-, 4-, 5- or 6-membered hydrocarbon ring,
R9 is —N(R11)R12,
wherein
R11 and R12 together and with inclusion of the nitrogen atom to which they are bonded, form a heterocyclic ring selected from the group consisting of a pyrrolidin-2,5-dione-1-yl-, isoindol-1,3-dione-2-yl-, 2-oxo-2,3-dihydro-1H-indol-1-yl-, pyrrolidin-2-one-1-yl-, piperidin-2,6-dione-1-yl-, morpholin-3,5-dione-4-yl-, thiomorpholin-3,5-dione-4-yl-, thiomorpholine-1-oxide-3,5-dione-4-yl- and a thiomorpholine-1,1-dioxide-3,5-dione-4-yl-ring; and
n is 1 or 2;
or a stereoisomer of the compound.

1-3-Alkyl is a straight-chain alkyl radical having 1 to 3 carbon atoms. Examples are the propyl, ethyl and methyl radicals.

1-2C-Alkyl is a straight-chain alkyl radical having 1 to 2 carbon atoms. Examples are the ethyl and methyl radicals.

1-2C-Alkoxy is a radical, which in addition to the oxygen atom, contains a straight-chain alkyl radical having 1 to 2 carbon atoms. Examples are the ethoxy and the methoxy radicals.

1-2C-Alkoxy which is completely or predominantly substituted by fluorine is, for example, the perfluoroethoxy, the 1,2,2-trifluoroethoxy, the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-2C-alkoxy group are replaced by fluorine atoms.

3-5C-Cycloalkoxy stands for cyclopropyloxy, cyclobutyloxy or cyclopentyloxy.

3-5C-Cycloalkylmethoxy stands for cyclopropylmethoxy, cyclobutylmethoxy or cyclopentylmethoxy.

As spiro-linked 5- or 6-membered hydrocarbon rings may be mentioned the cyclopentane and the cyclohexane ring.

As spiro-linked 3-, 4-, 5- or 6-membered hydrocarbon rings may be mentioned the cyclopropane, the cyclobutane, the cyclopentane and the cyclohexane ring.

In a preferred embodiment, the invention relates to a compound of formula 1, wherein R1 represents a phenyl derivative of formulae (a) or (b)

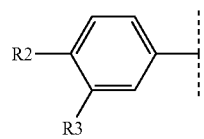

(a)

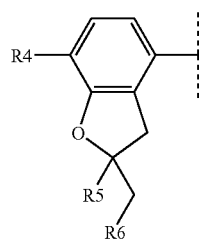

(b)

wherein
R2 is selected from the group consisting of 1-2C-alkoxy and 1-2C-alkoxy which is completely or predominantly substituted by fluorine;
R3 is selected from the group consisting of 1-2C-alkoxy, 3-5C-cycloalkoxy, 3-5C-cycloalkylmethoxy and 1-2C-alkoxy which is completely or predominantly substituted by fluorine;
R4 is selected from the group consisting of 1-2C-alkoxy and 1-2C-alkoxy which is completely or predominantly substituted by fluorine;
R5 is 1-2C-alkyl and
R6 is selected from the group consisting of hydrogen and 1-2C-alkyl;
or R5 and R6 together and with inclusion of the two carbon atoms, to which they are bonded, form a spiro-linked 5- or 6-membered hydrocarbon ring;
R7 is 1-3C-alkyl and
R8 is 1-3C-alkyl
or R7 and R8 together with the carbon atom, to which they are bonded, form a spiro-linked 3-, 4-, 5- or 6-membered hydrocarbon ring,
R9 is —N(R11)R12,
wherein
R11 and R12 together and with inclusion of the nitrogen atom to which they are bonded, form a heterocyclic ring selected from the group consisting of a pyrrolidin-2,5-dione-1-yl-, isoindol-1,3-dione-2-yl-, pyrrolidin-2-one-1-yl-, piperidin-2,6-dione-1-yl-, morpholin-3,5-dione-4-yl-, thiomorpholin-3,5-dione-4-yl-, thiomorpholine-1-oxide-3,5-dione-4-yl- and thiomorpholine-1,1-dioxide-3,5-dione-4-yl-ring; and
n is 1 or 2;
or a stereoisomer of the compound.

In a further preferred embodiment, the invention relates to a compound of formula 1, wherein R1 represents a phenyl derivative of formulae (a) or (b)

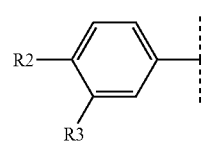

(a)

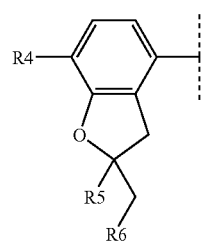

(b)

wherein
R2 is selected from the group consisting of 1-2C-alkoxy and 1-2C-alkoxy which is completely or predominantly substituted by fluorine;
R3 is selected from the group consisting of 1-2C-alkoxy and 1-2C-alkoxy which is completely or predominantly substituted by fluorine;
R4 is selected from the group consisting of 1-2C-alkoxy and 1-2C-alkoxy which is completely or predominantly substituted by fluorine;
R5 is 1-2C-alkyl and
R6 is selected from the group consisting of hydrogen and 1-2C-alkyl,
or R5 and R6 together and with inclusion of the two carbon atoms, to which they are bonded, form a spiro-linked 5- or 6-membered hydrocarbon ring;
R7 is 1-3C-alkyl and
R8 is 1-3C-alkyl
or R7 and R8 together with the carbon atom, to which they are bonded, form a spiro-linked 5- or 6-membered hydrocarbon ring;
R9 is —N(R11)R12,
wherein
R11 and R12 together and with inclusion of the nitrogen atom to which they are bonded, form a heterocyclic ring selected from the group consisting of a pyrrolidin-2,5-dione-1-yl-, isoindol-1,3-dione-2-yl-, 2-oxo-2,3-dihydro-1H-indol-1-yl-, pyrrolidin-2-one-1-yl-, piperidin-2,6-dione-1-yl-, morpholin-3,5-dione-4-yl-, thiomorpholin-3,5-dione-4-yl-, thiomorpholine-1-oxide-3,5-dione-4-yl- and thiomorpholine-1,1-dioxide-3,5-dione-4-yl-ring; and
n is 1 or 2;
or a stereoisomer of the compound.

In a further preferred embodiment, the invention relates to a compound of formula 1, wherein R1 represents a phenyl derivative of formulae (a) or (b)

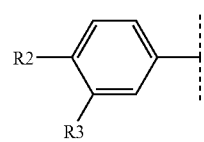

(a)

-continued

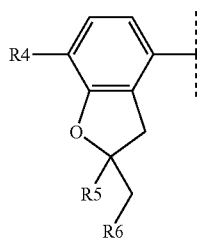
(b)

wherein
- R2 is selected from the group consisting of 1-2C-alkoxy and 1-2C-alkoxy which is completely or predominantly substituted by fluorine;
- R3 is selected from the group consisting of 1-2C-alkoxy and 1-2C-alkoxy which is completely or predominantly substituted by fluorine;
- R4 is selected from the group consisting of 1-2C-alkoxy and 1-2C-alkoxy which is completely or predominantly substituted by fluorine;
- R5 is 1-2C-alkyl and
- R6 is selected from the group consisting of hydrogen and 1-2C-alkyl,
  or R5 and R6 together and with inclusion of the two carbon atoms, to which they are bonded, form a spiro-linked 5- or 6-membered hydrocarbon ring;
- R7 is 1-3C-alkyl and
- R8 is 1-3C-alkyl
  or R7 and R8 together with the carbon atom, to which they are bonded, form a spiro-linked 5- or 6-membered hydrocarbon ring;
- R9 is —N(R11)R12,
  wherein
  R11 and R12 together and with inclusion of the nitrogen atom to which they are bonded, form a heterocyclic ring selected from the group consisting of a pyrrolidin-2,5-dione-1-yl-, isoindol-1,3-dione-2-yl-, pyrrolidin-2-one-1-yl-, piperidin-2,6-dione-1-yl-, morpholin-3,5-dione-4-yl-, thiomorpholin-3,5-dione-4-yl-, thiomorpholine-1-oxide-3,5-dione-4-yl- and thiomorpholine-1,1-dioxide-3,5-dione-4-yl-ring; and
- n is 1 or 2;
or a stereoisomer of the compound.

In a further preferred embodiment, the invention relates to a compound of formula 1, wherein
R1 represents a phenyl derivative of formulae (a) or (b)

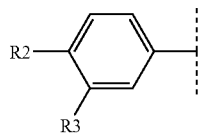
(a)

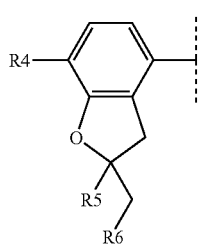
(b)

wherein
- R2 is selected from the group consisting of 1-2C-alkoxy and 1-2C-alkoxy which is completely or predominantly substituted by fluorine;
- R3 is selected from the group consisting of 1-2C-alkoxy and 1-2C-alkoxy which is completely or predominantly substituted by fluorine;
- R4 is selected from the group consisting of 1-2C-alkoxy and 1-2C-alkoxy which is completely or predominantly substituted by fluorine;
- R5 is methyl and
- R6 is hydrogen,
  or R5 and R6 together and with inclusion of the two carbon atoms, to which they are bonded, form a spiro-linked 5- or 6-membered hydrocarbon ring;
- R7 is 1-3C-alkyl and
- R8 is 1-3C-alkyl;
- R9 is —N(R11)R12,
  wherein
  R11 and R12 together and with inclusion of the nitrogen atom to which they are bonded, form a heterocyclic ring selected from the group consisting of a pyrrolidin-2,5-dione-1-yl-, morpholin-3,5-dione-4-yl-, thiomorpholin-3,5-dione-4-yl- and thiomorpholine-1,1-dioxide-3,5-dione-4-yl-ring; and
- n is 1 or 2;
or a stereoisomer of the compound.

In a further preferred embodiment, the invention relates to compounds of formula 1, wherein
R1 represents a phenyl derivative of formulae (a) or (b)

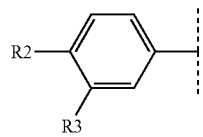
(a)

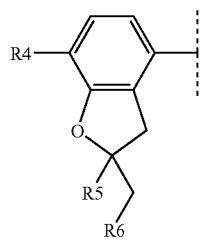
(b)

wherein
- R2 is methoxy;
- R3 is methoxy;
- R4 is methoxy;
- R5 is methyl;
- R6 is hydrogen,
  or R5 and R6 together and with inclusion of the two carbon atoms, to which they are bonded, form a spiro-linked 5- or 6-membered hydrocarbon ring;
- R7 is methyl;
- R8 is methyl;
- R9 is —N(R11)R12,
  wherein
  R11 and R12 together and with inclusion of the nitrogen atom to which they are bonded, form a heterocyclic ring selected from the group consisting of a pyrrolidin-2,5-dione-1-yl-, morpholin-3,5-dione-4-yl- and a thiomorpholin-3,5-dione-4-yl-ring; and
- n is 1.

In a further preferred embodiment, the invention relates to a compound of formula 1 or a stereoisomer thereof, wherein R1 represents a phenyl derivative of formula (a) and R2, R3, R7, R8, R9 and n are as defined above.

In a further preferred embodiment, the invention relates to a compound of formula 1 or a stereoisomer thereof, wherein R1 represents a phenyl derivative of formula (a), R2 is methoxy, R3 is methoxy and R7, R8, R9 and n are as defined above.

In a further preferred embodiment, the invention relates to a compound of formula 1, wherein R1 represents a phenyl derivative of formula (a), R7 is methyl, R8 is methyl and R2, R3, R9 and n are as defined above.

In a further preferred embodiment, the invention relates to a compound of formula 1, wherein R1 represents a phenyl derivative of formula (a), R2 is methoxy, R3 is methoxy, R7 is methyl, R8 is methyl, and R9 and n are as defined above.

In a further preferred embodiment, the invention relates to a compound of formula 1 or a stereoisomer thereof, wherein R1 represents a phenyl derivative of formula (a), n is 1 and R2, R3, R7, R8 and R9 are as defined above.

In a further preferred embodiment, the invention relates to a compound of formula 1, wherein R1 represents a phenyl derivative of formula (a), R2 is methoxy, R3 is methoxy, n is 1 and R7, R8 and R9 are as defined above.

In a further preferred embodiment, the invention relates to a compound of formula 1, wherein R1 represents a phenyl derivative of formula (a), R2 is methoxy, R3 is methoxy, R7 is methyl, R8 is methyl, n is 1 and R9 is as defined above.

In a further preferred embodiment, the invention relates to a compound of formula 1 or a stereoisomer thereof, wherein R1 represents a phenyl derivative of formula (a), R9 is morpholin-3,5-dione-4-yl and R2, R3, R7, R8 and n are as defined above.

In a further preferred embodiment, the invention relates to a compound of formula 1 or a stereoisomer thereof, wherein R1 represents a phenyl derivative of formula (a), R9 is morpholin-3,5-dione-4-yl, n is 1 and R2, R3, R7 and R8 are as defined above.

In a further preferred embodiment, the invention relates to a compound of formula 1 or a stereoisomer thereof, wherein R1 represents a phenyl derivative of formula (a), R9 is pyrrolidin-2,5-done-1-yl and R2, R3, R7, R8 and n are as defined above.

In a further preferred embodiment, the invention relates to a compound of formula 1 or a stereoisomer thereof, wherein R1 represents a phenyl derivative of formula (a), R9 is pyrrolidin-2,5-dione-1-yl, n is 1 and R2, R3, R7 and R8 are as defined above.

In a further preferred embodiment, the invention relates to a compound of formula 1 or a stereoisomer thereof, wherein R1 represents a phenyl derivative of formula (b) and R4, R5; R6, R7, R8, R9 and n are as defined above.

In a further preferred embodiment, the invention relates to a compound of formula 1 or a stereoisomer thereof, wherein R1 represents a phenyl derivative of formula (b), R4 is methoxy, R5 is methyl, R6 is hydrogen and R7, R8 and R9 are as defined above.

In a further preferred embodiment, the invention relates to a compound of formula 1 or a stereoisomer thereof, wherein R1 represents a phenyl derivative of formula (b), R4 is methoxy, R5 and R6 together and with inclusion of the two carbon atoms to which they are bonded form a spiro-linked cyclopentane ring and R7, R8 and R9 are as defined above.

In a further preferred embodiment, the invention relates to a compound of formula 1 or a stereoisomer thereof, wherein R1 represents a phenyl derivative of formula (b), R7 is methyl, R8 is methyl, and R4, R5, R6, R9 and n are as defined above.

In a further preferred embodiment, the invention relates to a compound of formula 1, wherein R1 represents a phenyl derivative of formula (b), R4 is methoxy, R5 is methyl, R6 is hydrogen, R7 is methyl, R8 is methyl and R9 and n are as defined above.

In a further preferred embodiment, the invention relates to a compound of formula 1, wherein R1 represents a phenyl derivative of formula (b), R4 is methoxy, R5 and R6 together and with inclusion of the two carbon atoms to which they are bonded form a spiro-linked cyclopentane ring, R7 is methyl, R8 is methyl and R9 and n are as defined above.

In a further preferred embodiment, the invention relates to a compound of formula 1 or a stereoisomer thereof, wherein R1 represents a phenyl derivative of formula (b), n is 1 and R4, R5, R6, R7, R8 and R9 are as defined above.

In a further preferred embodiment, the invention relates to a compound of formula 1 or a stereoisomer thereof, wherein R1 represents a phenyl derivative of formula (b), R4 is methoxy, R5 is methyl, R6 is hydrogen, n is 1 and R7, R8 and R9 are as defined above.

In a further preferred embodiment, the invention relates to a compound of formula 1 or a stereoisomer thereof, wherein R1 represents a phenyl derivative of formula (b), R4 is methoxy, R5 and R6 together and with inclusion of the two carbon atoms to which they are bonded form a spiro-linked cyclopentane ring, n is 1 and R7, R8 and R9 are as defined above.

In a further preferred embodiment, the invention relates to a compound of formula 1, wherein R1 represents a phenyl derivative of formula (b), R4 is methoxy, R5 is methyl, R6 is hydrogen, R7 is methyl, R8 is methyl, n is 1 and R9 is as defined above.

In a further preferred embodiment, the invention relates to a compound of formula 1, wherein R1 represents a phenyl derivative of formula (b), R4 is methoxy, R5 and R6 together and with inclusion of the two carbon atoms to which they are bonded form a spiro-linked cyclopentane ring, R7 is methyl, R8 is methyl, n is 1 and R9 is as defined above.

In a further preferred embodiment, the invention relates to a compound of formula 1 or a stereoisomer thereof, wherein R1 represents a phenyl derivative of formula (b), R9 is morpholin-3,5-dione-4-yl, and R4, R5, R6, R7, R8 and n are as defined above In a further preferred embodiment, the invention relates to a compound of formula 1 or a stereoisomer thereof, wherein R1 represents a phenyl derivative of formula (b), R9 is morpholin-3,5-dione-4-yl, n is 1 and R4, R5, R6, R7 and R8 are as defined above.

In a further preferred embodiment, the invention relates to a compound of formula 1 or a stereoisomer thereof, wherein R1 represents a phenyl derivative of formula (b), R9 is pyrrolidin-2,5-dione-1-yl, and R4, R5, R6, R7, R8 and n are as defined above.

In a further preferred embodiment, the invention relates to a compound of formula 1 or a stereoisomer thereof, wherein R1 represents a phenyl derivative of formula (b), R9 is pyrrolidin-2,5-dione-1-yl, n is 1 and R4, R5, R6, R7 and R8 are as defined above.

It is to be understood that the invention covers all combinations of substituent groups referred to hereinabove. In particular, the invention covers all combinations of preferred groups described herein.

The compounds of the invention may contain, e.g. when isolated in crystalline form, varying amounts of solvents. Included within the scope of the invention are, therefore, all solvates of the compounds of formula 1 and the stereoisomers thereof. Hydrates are a preferred example of said solvates.

The compounds of formula 1 according to the invention include stereoisomers. In case R7 and R8 represent different groups and/or R5 and CH$_2$R6 represent different groups, the compounds according to the invention have one or two stereogenic centers. Each of said stereogenic centers may have the absolute configuration R or the absolute configuration S (according to Cahn, Ingold and Prelog).

Accordingly, the stereoisomers (4R) and (4S) in case of a compound of formula Ia* and the stereoisomers (2R,4R), (2R,4S), (2S,4R) and (2S,4R) in case of a compound of formula 1b*

(1a*)

(1b*)

are part of the invention (the numbers refer to the atoms indicated in formulae Ia* and Ib*).

The invention further includes all mixtures of the stereoisomers mentioned above independent of the ratio, including the racemates.

Some of the compounds of formula 1 or stereoisomers thereof may exist in different crystalline forms (polymorphs), which are within the scope of the invention.

The invention further relates to compounds of formula 4, which are key intermediates in the process of producing the compounds of formula 1 according to the invention as described hereinafter.

The invention therefore also relates to a compound of formula 4, (4)

wherein
R1 represents a phenyl derivative of formulae (a) or (b)

(a)

(b)

wherein
R2 is selected from the group consisting of 1-2C-alkoxy and 1-2C-alkoxy which is completely or predominantly substituted by fluorine;
R3 is selected from the group consisting of 1-2C-alkoxy, 3-5C-cycloalkoxy, 3-5C-cycloalkylmethoxy and 1-2C-alkoxy which is completely or predominantly substituted by fluorine;
R4 is selected from the group consisting of 1-2C-alkoxy and 1-2C-alkoxy which is completely or predominantly substituted by fluorine;
R5 is 1-2C-alkyl and
R6 is selected from the group consisting of hydrogen and 1-2C-alkyl,
or R5 and R6 together and with inclusion of the two carbon atoms, to which they are bonded, form a spiro-linked 5- or 6-membered hydrocarbon ring;
R7 is 1-3C-alkyl and
R8 is 1-3C-alkyl
or R7 and R8 together with the carbon atom, to which they are bonded, form a spiro-linked 3-, 4-, 5- or 6-membered hydrocarbon ring;
a salt thereof, a stereoisomer thereof or a salt of the stereoisomer thereof.

Salts of the compounds of formula 4 or the salts of the stereoisomers thereof include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxybenzoyl)benzoates, butyrates, sulfosalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates. Of these, hydrochlorides are preferred.

Examples of salts with bases include, but are not limited to, lithium, sodium, potassium, calcium, aluminum, magnesium, titanium, ammonium, meglumine and guanidinium salts.

The salts include water-insoluble and, particularly, water-soluble salts.

The compounds of formula 4, the salts, the stereoisomers and the salts of the stereoisomers thereof may contain, e.g. when isolated in crystalline form, varying amounts of solvents. Included within the scope of the invention are, therefore, all solvates of the compounds of formula 4, as well as the solvates of the salts, the stereoisomers and the salts of the stereoisomers of the compounds of formula 4.

In a preferred embodiment the invention relates to a compound of formula 4, wherein R1 represents a phenyl derivative of formulae (a) or (b)

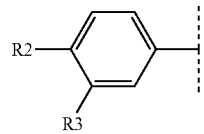

(a)

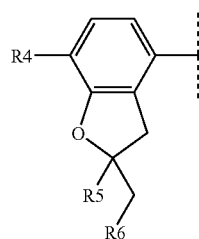

(b)

wherein
  R2 is selected from the group consisting of 1-2C-alkoxy and 1-2C-alkoxy which is completely or predominantly substituted by fluorine;
  R3 is selected from the group consisting of 1-2C-alkoxy and 1-2C-alkoxy which is completely or predominantly substituted by fluorine;
  R4 is selected from the group consisting of 1-2C-alkoxy and 1-2C-alkoxy which is completely or predominantly substituted by fluorine;
  R5 is 1-2C-alkyl and
  R6 is selected from the group consisting of hydrogen and 1-2C-alkyl,
  or R5 and R6 together and with inclusion of the two carbon atoms, to which they are bonded, form a spiro-linked 5- or 6-membered hydrocarbon ring;
  R7 is 1-3C-alkyl and
  R8 is 1-3C-alkyl
  or R7 and R8 together with the carbon atom, to which they are bonded, form a spiro-linked 5- or 6-membered hydrocarbon ring;
a salt thereof, a stereoisomer thereof or a salt of the stereoisomer thereof.

In another preferred embodiment, the invention relates to a compound of formula 4, wherein R1 represents a phenyl derivative of formulae (a) or (b)

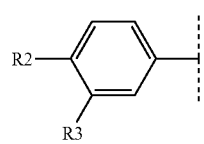

(a)

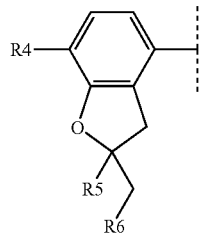

(b)

wherein
  R2 is selected from the group consisting of 1-2C-alkoxy and 1-2C-alkoxy which is completely or predominantly substituted by fluorine;
  R3 is selected from the group consisting of 1-2C-alkoxy and 1-2C-alkoxy which is completely or predominantly substituted by fluorine;
  R4 is selected from the group consisting of 1-2C-alkoxy and 1-2C-alkoxy which is completely or predominantly substituted by fluorine;
  R5 is methyl and
  R6 is hydrogen,
  or R5 and R6 together and with inclusion of the two carbon atoms, to which they are bonded, form a spiro-linked 5- or 6-membered hydrocarbon ring;
  R7 is 1-3C-alkyl and
  R8 is 1-3C-alkyl;
a salt thereof, a stereoisomer thereof or a salt of the stereoisomer thereof.

In a further preferred embodiment the invention relates to compounds of formula 4, wherein R1 represents a phenyl derivative of formulae (a) or (b)

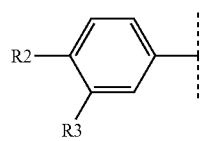

(a)

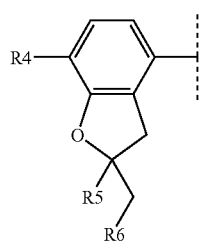

(b)

wherein
  R2 is methoxy;
  R3 is methoxy;
  R4 is methoxy;
  R5 is methyl;
  R6 is hydrogen,
  or R5 and R6 together and with inclusion of the two carbon atoms, to which they are bonded, form a spiro-linked 5- or 6-membered hydrocarbon ring;
  R7 is methyl;
  R8 is methyl;
or a salt thereof.

In a further preferred embodiment, the invention relates to a compound of formula 4, wherein R1 represents a phenyl derivative of formula (a), R2 is methoxy, R3 is methoxy, R7 is methyl and R8 is methyl, or a salt thereof.

In a further preferred embodiment, the invention relates to a compound of formula 4, wherein R1 represents a phenyl derivative of formula (b), R4 is methoxy, R5 is methyl, R6 is hydrogen, R7 is methyl and R8 is methyl, or a salt thereof.

In a further preferred embodiment, the invention relates to a compound of formula 4, wherein R1 represents a phenyl derivative of formula (b), R4 is methoxy, R5 and R6 together and with inclusion of the two carbon atoms, to which they are bonded, form a spiro-linked cyclopentane-ring, R7 is methyl and R8 is methyl, or a salt thereof.

The compounds of formula 4 include stereoisomers. In case R7 and R8 represent different groups and/or R5 and CH$_2$R6 represent different groups, the compounds of formula 4 have one or two stereogenic centers. Each of said stereogenic centers may have the absolute configuration R or the absolute configuration S (according to Cahn, Ingold and Prelog).

Accordingly, the stereoisomers (4R) and (4S) in case of a compound of formula 4a* and the stereoisomers (2R,4R), (2R,4S), (2S,4R) and (2S,4R) in case of a compound of formula 4b*

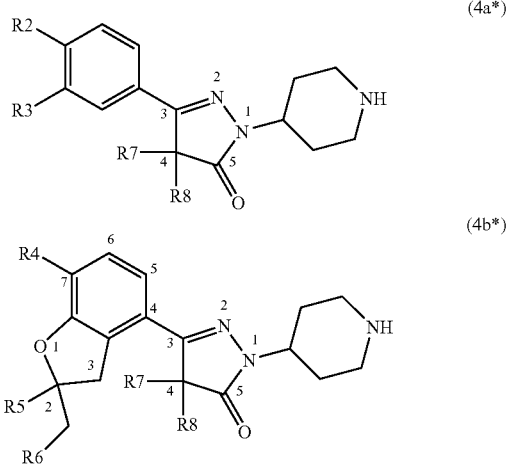

are part of the invention (the numbers refer to the atoms indicated in formulae 4a* and 4b*).

The invention further includes all mixtures of the stereoisomers mentioned above independent of the ratio, including the racemates.

The compounds of formula 1 and the compounds of formula 4 according to the invention can be prepared as follows.

As shown in reaction scheme 1 the compounds of formula 1, wherein R1, R7, R8 and R9 have the above-mentioned meanings and n is 1 can be obtained by reacting a corresponding compound of formula 2 with a compound of formula R9—H, wherein R9 has the above-mentioned meanings in an appropriate solvent, such as, for example N,N-dimethylformamide, 1-methyl-pyrrolidin-2-one, ethanol, 2-propanol, 1-propanol, butanol, acetonitril or tetrahydrofurane, preferably in the presence of a base, such as, for example potassium carbonate, sodium carbonate or diisopropylethylamine and preferably at raised temperature up to the boiling point of the solvent being used.

The compounds of formula 2, wherein R1, R7 and R8 have the above-mentioned meanings can be obtained by reacting a corresponding compound of formula 4 with chloroacetyl-chloride or chloroacetic anhydride in an inert solvent, such as, for example dichloromethane, chloroform, toluene, tetrahydrofurane or acetonitril, preferably in the presence of a base, such as, for example triethylamine or diisopropylethylamine, preferably at a temperature between 0° C. and ambient temperature.

The compounds of formula 1, wherein R1, R7, R8 and R9 have the above-mentioned meanings and n is 2 can be obtained by reacting a corresponding compound of formula 3 with a compound of formula R9—H, wherein R9 has the above-mentioned meanings in an appropriate solvent, such as, for example N,N-dimethylformamide, 1-methyl-pyrrolidin-2-one, methanol, ethanol, tetrahydrofurane, dichloromethane or toluene, preferably in the presence of an base, such as, for example potassium carbonate, sodium carbonate, diisopropylethylamine or triethylamine, and preferably at raised temperature up to the boiling point of the solvent being used.

The compounds of formula 3, wherein R1, R7 and R8 have the above-mentioned meanings can be prepared by reacting a corresponding compound of formula 4 with prop-2-enoyl chloride in an inert solvent, such as, for example dichloromethane, chloroform, acetonitril or tetrahydrofurane, preferably in the presence of a base, such as, for example triethylamine or diisopropylethylamine. The reaction is preferably carried out at ambient temperature.

The compounds of formula 4, wherein R1, R7 and R8 have the above-mentioned meanings can be prepared by reacting a corresponding compound of formula 5 with an in 4-position activated and in 1-position protected piperidine-derivative, such as, for example tert-butyl 4-(toluene-4-sulfonyloxy)piperidine-1-carboxylate or tert-butyl 4-(methanesulfonyloxy)-piperidine-1-carboxylate in an inert solvent, such as, for example N,N-dimethylformamide, 1-methyl-pyrrolidin-2-one or dioxane, in the presence of a strong base, such as, for example sodium ethoxide, potassium tert-butoxide, sodium hydride, and preferably at raised temperature, such as, for example 80 to 150° C.

Alternatively, the compounds of formula 4, wherein R1, R7 and R8 have the above-mentioned meanings can be prepared by reacting a corresponding compound of formula 6 with piperidin-4-ylhydrazine dihydrochloride in a methanol/water solvent system, preferably at raised temperatures, especially at the boiling point of the solvent system being used.

The compounds of formula 5, wherein R1, R7 and R8 have the above-mentioned meanings can be obtained by reacting an appropriately substituted α,α-disubstituted-β-oxobenzene propionic acid ester of formula 6 with hydrazine hydrate in an appropriate solvent, such as, for example an alcohol like ethanol or methanol, preferably at raised temperature, especially at the boiling point of the solvent being used. The ester of the α,α-disubstituted-β-oxobenzene propionic acid ester may be a 1-4C-alkyl ester; particularly preferred is—as shown in reaction scheme 1—the methyl ester.

The compounds of formula 6, wherein R1, R7 and R8 have the above-mentioned meanings can be prepared by reacting an activated benzoic acid derivative of formula 8, wherein R1 has the above-mentioned meanings with an ester of formula 7, wherein R7 and R8 have the above-mentioned meanings, in an inert solvent, such as, for example tetrahydrofurane, diethyl ether, toluene, N,N-dimethylformamide or 1-methyl-pyrrolidin-2-one, in the presence of a strong base, such as for example lithium diisopropylamine, butyl lithium or sodium hydride, at low temperatures, preferably below −40° C.

Suitable esters of formula 7 are for example methyl 2-methylproponate, methyl-2-methylbutanoate, methyl-2-ethylbutanoate, methyl 2-methylpentanoate and methyl cyclopentancarboxylate.

The esters of formula 7 are commercially available or can be prepared according to procedures known in the art.

The activated benzoic acid derivatives of formula 8 can be obtained, for example, according to the procedures described in the international patent applications WO92/12961, WO94/02465, WO95/01338 and WO96/03399.

An alternative synthesis route to compounds of formula 5 is described in the European patent application EP0126651.

Reaction scheme 1:

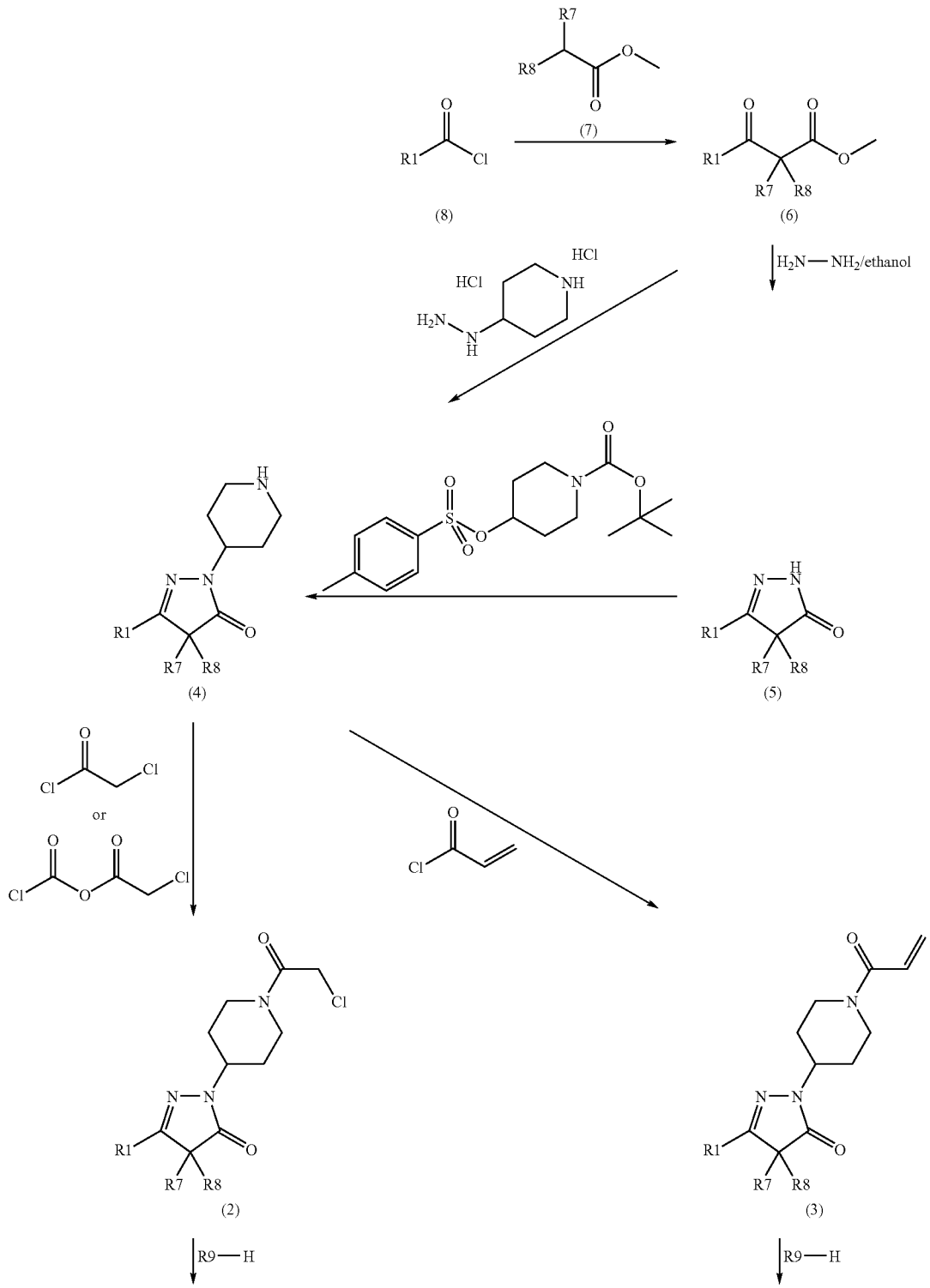

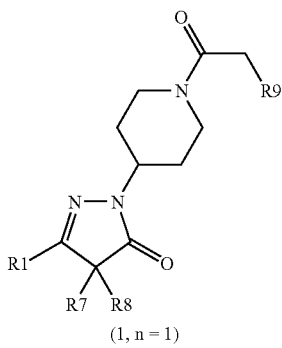

(1, n = 1)

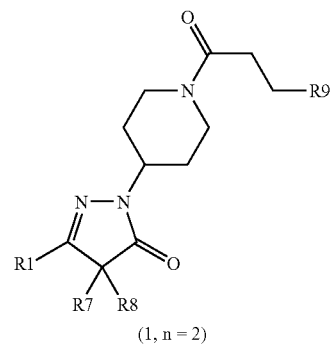

(1, n = 2)

Compounds of formula 1 can be converted into further compounds of formula 1 by methods known in the art. For example
a compound of formula 1, wherein R9 is a thiomorpholine-1-oxide-3,5-dione-4-yl- or a thiomorpholine-1,1-dioxide-3,5-dione-4-yl-ring can be prepared from a compound of formula 1, wherein R9 is a thiomorpholine-3,5-dione-4-yl-ring by an oxidation reaction, for example by using 3-chloroperbenzoic acid in dichloromethane as an oxidant.

A further possibility to prepare compounds of formula 1 is to use a temporarily protective group in order to introduce a specific substituent at the end of a reaction sequence. This method can be advantageously used, for example, to introduce different alkoxy groups in the position of the R3 substituent. Examples 5, 6 and 7 have been prepared using such a method; here, the benzyl group served as a temporarily protective group for a hydroxyl group in R3 position.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts of the compounds of formula 4 and the stereoisomers thereof can be obtained by dissolving the free compound in a suitable solvent (for example a ketone such as acetone, methylethylketone or methylisobutylketone, an ether such as diethyl ether, tetrahydrofurane or dioxane, a chlorinated hydrocarbon such as methylene chloride or chloroform, a low molecular weight aliphatic alcohol such as methanol, ethanol or isopropanol, a low molecular weight aliphatic ester such as ethyl acetate or isopropyl acetate, or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds according to the invention can be obtained e.g. by asymmetric synthesis, by using chiral starting compounds in synthesis and by splitting up enantiomeric and diasteriomeric mixtures obtained in synthesis. Preferably, the pure diastereomeric and pure enantiomeric compounds of the invention are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

As will be appreciated by persons skilled in the art, the invention is not limited to the particular embodiments described herein, but covers all modifications that are within the spirit and scope of the invention as defined by the appended claims.

All patents, patent applications, publications, test methods and other materials cited herein are incorporated by reference in their entireties.

The following examples illustrate the invention in greater detail, without restricting it. Further compounds according to the invention, of which the preparation is not explicitly described, can be prepared in an analogous way.

The compounds, which are mentioned in the examples and the stereoisomers thereof represent preferred embodiments of the invention.

EXAMPLES

The following abbreviations are used: min: minutes, h: hour(s), DCM: dichloromethane, THF: tetrahydrofurane, EA: ethyl acetate, DMF: N,N-dimethylformamide, M.p.: melting point, RT: room temperature (20 to 25° C.), MS: mass spectrometry and calc: calculated.

Final Products

1. 4-(2-{4-[3-(3,4-dimethoxyphenyl)-4,4-dimethyl-5-oxo-4,5-dihydro-1H-pyrazol-1-yl]piperidin-1-yl}-2-oxoethyl)morpholine-3,5-dione 1.0 g 2-[1-(chloroacetyl)piperidin-4-yl]-5-(3,4-dimethoxyphenyl)-4,4-dimethyl-2,4-dihydro-3H-pyrazol-3-one (compound A1), 0.5 g morpholine-3,5-dione and 1.0 g $K_2CO_3$ in 20 ml of DMF is heated for 17 h at 80-100° C. The DMF is removed in vacuo and the residue dissolved in 70 ml of DCM, washed four times with 30 ml of water and 20 ml of 0.5 M $H_2SO_4$. The DCM layer is dried over $MgSO_4$ and concentrated in vacuo. The title product is crystallized from diethyl ether.

M.p. 156-157° C.

2. 1-(2-{4-[3-(3,4-dimethoxyphenyl)-4,4-dimethyl-5-oxo-4,5-dihydro-1H-pyrazol-1-yl]piperidin-1-yl}-2-oxoethyppyrrolidine-2,5-dione 7.4 g 241-(chloroacetyppiperidin-4-y11-5-(3,4-dimethoxyphenyl)-4,4-dimethyl-2,4-dihydro-3H-pyrazol-3-one (compound A1) and 3.6 g succinimide are suspended in 50 ml of 2-propanol and heated to 50° C. 5.1 g potassium carbonate are added in portions during 1 h. After adding potassium carbonate the reaction mixture is stirred for 30 min at 50° C., then 3-4 h at 75° C. until the reaction is complete. After stirring for 3-4 h at 75° C., the heating is turned off and the mixture is allowed to cool down slowly to RT. 100 ml of water is added, the mixture is stirred for 0.5 h at RT and the crystallized product is filtered. The product is dried at 50° C. in a vacuum dryer.

M.p. 218-220° C.

3. 1-(2-{4-[3-(3,4-diethoxyphenyl)-4,4-dimethyl-5-oxo-4,5-dihydro-1H-pyrazol-1-yl]piperidin-1-yl}-2-oxoethyppyrrolidine-2,5-dione Prepared analogously as described for example 1 using 2-[1-(chloroacetyl)piperidin-4-yl]-5-(3,4-diethoxyphenyl)-4,4-dimethyl-2,4-dihydro-3H-pyrazol-3-one (compound A2) and succinimide as starting compounds.

M.p. 211-213° C.

4. 1-[2-(4-{3-[3-(cyclopropylmethoxy)-4-(difluoromethoxy)phenyl]-4,4-dimethyl-5-oxo-4,5-dihydro-1H-pyrazol-1-yl}piperidin-1-yl)-2-oxoethyl]pyrrolidine-2,5-dione Prepared analogously as described for example 1 using 2-[1-(chloroacetyl)piperidin-4-yl]-5-[3-(cyclopropylmethoxy)-4-(difluoromethoxy)phenyl]-4,4-dimethyl-2,4-dihydro-3H-pyrazol-3-one (compound A3) and succinimide as starting compounds.

M.p. 104-109° C.

5. 1-[2-(4-{3-[3-(cyclopropylmethoxy)-4-methoxyphenyl]-4,4-dimethyl-5-oxo-4,5-dihydro-1H-pyrazol-1-yl}piperidin-1-yl)-2-oxoethyl]pyrrolidine-2,5-dione A mixture of 1 g 1-(2-{4-[3-(3-hydroxy-4-methoxyphenyl)-4,4-dimethyl-5-oxo-4,5-dihydro-1H-pyrazol-1-yl]piperidin-1-yl}-2-oxoethyppyrrolidine-2,5-dione (compound A4), 0.7 g of bromomethylcyclopropane and 1 g of potassium carbonate in 100 ml of acetonitril is refluxed for 8 h after which the solvent is evaporated. The residue is partitioned between water and ethyl acetate, the organic layer is dried over magnesium sulfate and the EA evaporated. The residue is crystallized from ethyl acetate.

M.p. 129-131° C.

6. 1-[2-(4-{3-[4-methoxy-3-(2,2,2-trifluoroethoxy)phenyl]-4,4-dimethyl-5-oxo-4,5-dihydro-1H-pyrazol-1-yl}piperidin-1-yl)-2-oxoethyl]pyrrolidine-2,5-dione Prepared analogously as described for example 5 using 1-(2-{4-[3-(3-hydroxy-4-methoxyphenyl)-4,4-dimethyl-5-oxo-4,5-dihydro-1H-pyrazol-1-yl]piperidin-1-yl}-2-oxoethyl)pyrrolidine-2,5-dione (compound A4) and 1,1,1-trifluoro-2-iodoethane as starting compounds.

M.p. 101-106° C.

7. 1-(2-{4-[3-(3-ethoxy-4-methoxyphenyl)-4,4-dimethyl-5-oxo-4,5-dihydro-1H-pyrazol-1-yl]piperidin-1-yl}-2-oxoethyl)pyrrolidine-2,5-dione Prepared analogously as described for example 5 using 1-(2-{4-[3-(3-hydroxy-4-methoxyphenyl)-4,4-dimethyl-5-oxo-4,5-dihydro-1H-pyrazol-1-yl]piperidin-1-yl}-2-oxoethyl)pyrrolidine-2,5-dione (compound A4) and iodoethane as starting compounds.

M.p. 186-187° C.

8. 1-(2-{4-[3-(7-methoxy-2,2-dimethyl-2,3-dihydro-1-benzofuran-4-yl)-4,4-dimethyl-5-oxo-4,5-dihydro-1H-pyrazol-1-yl]piperidin-1-yl}-2-oxoethyl)pyrrolidine-2,5-dione Prepared analogously as described for example 1 using 2-[1-(chloroacetyl)piperidin-4-yl]-5-(7-methoxy-2,2-dimethyl-2,3-dihydro-1-benzofuran-4-yl)-4,4-dimethyl-2,4-dihydro-3H-pyrazol-3-one (compound A5) and succinimide as starting compounds.

M.p. 214-215° C.

9. 1-(2-{4-[3-(7-methoxy-3H-spiro[1-benzofuran-2,1'-cyclopentan]-4-yl)-4,4-dimethyl-5-oxo-4,5-dihydro-1H-pyrazol-1-yl]piperidin-1-yl}-2-oxoethyl)pyrrolidine-2,5-dione Prepared analogously as described for example 1 using 2-[1-(chloroacetyl)piperidin-4-yl]-5-(7-methoxy-3H-spiro[1-benzofuran-2,1'-cyclopentan]-4-yl)-4,4-dimethyl-2,4-dihydro-3H-pyrazol-3-one (compound A6) and succinimide as starting compounds.

M.p. 220-222° C.

10. 1-(2-{4-[3-(3,4-dimethoxyphenyl)-4,4-diethyl-5-oxo-4,5-dihydro-1H-pyrazol-1-yl]piperidin-1-yl}-2-oxoethyl)pyrrolidine-2,5-dione The title compound may be prepared analogously as described for example 1 using 2-[1-(chloroacetyl)piperidin- 4-yl]-5-(3,4-dimethoxyphenyl)-4,4-diethyl-2,4-dihydro-3H-pyrazol-3-one (compound A7) and succinimide as starting compounds.

11. 1-(2-{4-[3-(3,4-dimethoxyphenyl)-4-methyl-5-oxo-4-propyl-4,5-dihydro-1H-pyrazol-1-yl]piperidin-1-yl}-2-oxoethyl)pyrrolidine-2,5-dione Prepared analogously as described for example 1 using 2-[1-(chloroacetyl)piperidin-4-yl]-5-(3,4-dimethoxyphenyl)-4-methyl-4-propyl-2,4-dihydro-3H-pyrazol-3-one (compound A8) and succinimide as starting compounds.
M.p. 167-169° C.

12. 1-(2-{4-[3-(3,4-dimethoxyphenyl)-4-ethyl-4-methyl-5-oxo-4,5-dihydro-1H-pyrazol-1-yl]piperidin-1-yl}-2-oxoethyl)pyrrolidine-2,5-dione Prepared analogously as described for example 1 using 2-[1-(chloroacetyl)piperidin-4-yl]-5-(3,4-dimethoxyphenyl)-4-ethyl-4-methyl-2,4-dihydro-3H-pyrazol-3-one (compound A9) and succinimide as starting compounds.
M.p. 121-124° C.

13. 1-(2-{4-[4-(3,4-dimethoxyphenyl)-1-oxo-2,3-diazaspiro[4.4]non-3-en-2-yl]piperidin-1-yl}-2-oxoethyl)pyrrolidine-2,5-dione Prepared analogously as described for example 1 using 2-[1-(chloroacetyl)piperidin-4-yl]-4-(3,4-dimethoxyphenyl)-2,3-diazaspiro[4.4]non-3-en-1-one (compound A10) and succinimide as starting compounds.
M.p. 186-189° C.

14. 2-(2-{4-[3-(3,4-dimethoxyphenyl)-4,4-dimethyl-5-oxo-4,5-dihydro-1H-pyrazol-1-yl]piperidin-1-yl}-2-oxoethyl)-1H-isoindole-1,3(2H)-dione Prepared analogously as described for example 1 using 2-[1-(chloroacetyl)piperidin-4-yl]-5-(3,4-dimethoxyphenyl)-4,4-dimethyl-2,4-dihydro-3H-pyrazol-3-one (compound A1) and phthalimide as starting compounds.
M.p. 209-211° C.

15. 1-(2-{4-[3-(3,4-Dimethoxy-phenyl)-4,4-dimethyl-5-oxo-4,5-dihydro-pyrazol-1-yl]-piperidin-1-yl}-2-oxo-ethylypiperidine-2,6-dione Prepared analogously as described for example 1 using 2-[1-(chloroacetyl)piperidin-4-yl]-5-(3,4-dimethoxyphenyl)-4,4-dimethyl-2,4-dihydro-3H-pyrazol-3-one (compound A1) and 2,6-dioxopiperidine as starting compounds.
M.p. 146-149° C.

16. 5-(3,4-dimethoxyphenyl)-4,4-dimethyl-2-{1-[(2-oxopyrrolidin-1-yl)acetyl]piperidin-4-yl}-2,4-dihydro-3H-pyrazol-3-one A mixture of 0.5 g of 5-(3,4-dimethoxyphenyl)-4,4-dimethyl-2-piperidin-4-yl-2,4-dihydro-3H-pyrazol-3-one hydrochloride (compound B1), 0.24 g of (2-oxo-pyrrolidin-1-yl)acetyl chloride and 0.5 ml of triethyl amine in 50 ml of dichloromethane is stirred for 30 min and washed subsequently with aqueous sodium carbonate. After drying over magnesium sulphate the solvent is evaporated and the residue purified by column chromatography [silica, ethyl acetate/methanol: 6:1(Vol/Vol)]. Crystallized from diethyl ether.
M.p. 125-131° C.

17. 4-(2-{4-[3-(3,4-dimethoxyphenyl)-4,4-dimethyl-5-oxo-4,5-dihydro-1H-pyrazol-1-yl]piperidin-1-yl}-2-oxoethyl)thiomorpholine-3,5-dione A mixture of 1 g 5-(3,4-dimethoxyphenyl)-2-(1-glycylpiperidin-4-yl)-4,4-dimethyl-2,4-dihydro-3H-pyrazol-3-one hydrochloride (compound F1), 0.3 g triethylamine, 0.34 g 2,6-dioxothiomorpholine and 0.83 g 1-(3-dimethylaminopropyl)-ethylcarbodiimide hydrochloride in 5 ml of dichloromethane is heated in a sealed cap for 10 min at 150° C. in a microwave. After cooling to RT, 100 ml of DCM is added and the resulting mixture is washed with water. After drying over magnesium sulphate and evaporating the solvent, the title compound is purified by column chromatography [silica, ethyl acetate]. The title compound is crystallised from diethyl ether.
M.p. 121-124° C.

18. 4-(2-{4-[3-(3,4-dimethoxyphenyl)-4,4-dimethyl-5-oxo-4,5-dihydro-1H-pyrazol-1-yl]piperidin-1-yl}-2-oxoethyl)thiomorpholine-3,5-dione 1,1-dioxide A solution of 0.5 g of 4-(2-{4-[3-(3,4-dimethoxyphenyl)-4,4-dimethyl-5-oxo-4,5-dihydro-1H-pyrazol-1-yl]piperidin-1-yl}-2-oxoethyl)thiomorpholine-3,5-dione (compound 17) in 20 ml of DCM is cooled to 0° C.; then 0.57 g 3-chloroperbenzoic acid is added. The resulting mixture is stirred for another 20 min and subsequently washed with aqueous sodium carbonate. The organic phase is dried over magnesium sulphate and the solvent evaporated. The title compound is crystallized from ethyl acetate.
M.p. 146-148° C.

19. 1-(3-{4-[3-(3,4-Dimethoxy-phenyl)-4,4-dimethyl-5-oxo-4,5-dihydro-pyrazol-1-yl]-piperidin-1-yl}-3-oxo-propyl)-pyrrolidine-2,5-dione A mixture of 1 g 5-(3,4-dimethoxyphenyl)-4,4-dimethyl-2-piperidin-4-yl-2,4-dihydro-3H-pyrazol-3-one hydrochloride (compound B1), 0.5 g prop-2-enoyl chloride and 1 ml of triethylamine in 100 ml of DCM is stirred for 30 min and subsequently washed with aqueous sodium carbonate. After drying over magnesium sulphate, the solvate is evaporated; the residue is dissolved in DMF, 1 g potassium carbonate and 0.3 g succinimide is added and the resulting mixture is heated for 4 h at 70° C. The solvent is removed by evaporation; the residue is dissolved in EA and washed with water. After drying over magnesium sulphate and evaporating the solvent, the title compound is crystallized from diethyl ether.
M.p. 207-209° C.

20. 1-(2-{4-[3-(3,4-Dimethoxy-phenyl)-4,4-dimethyl-5-oxo-4,5-dihydro-pyrazol-1-yl]-piperidin-1-yl}-2-oxo-ethyl)-1,3-dihydro-2H-indol-2-one 0.5 g 2-[1-(chloroacetyl)piperidin-4-yl]-5-(3,4-dimethoxyphenyl)-4,4-dimethyl-2,4-dihydro-3H-pyrazol-3-one (compound A1), 0.16 g 1,3-dihydro-2H-indol-2-one and 0.7 g $K_2CO_3$ in 20 ml of acetonitrile is heated to reflux for 10 h. The acetonitrile is removed in vacuo and the residue dissolved in 70 ml of ethyl acetate and washed four times with 30 ml of water. The organic layer is dried over $MgSO_4$ and concentrated in vacuo. The title product is isolated by column chromatography (silica gel, eluent: ethyl acetate to ethyl acetate/methanol 4:1).
M.p. 178° C.

Starting Compounds

A1. 2-[1-(chloroacetyl)piperidin-4-yl]-5-(3,4-dimethoxyphenyl)-4,4-dimethyl-2,4-dihydro-3H-pyrazol-3-one 157.1 g 5-(3,4-dimethoxyphenyl)-4,4-dimethyl-2-piperidin-4-yl-2,4-dihydro-3H-pyrazol-3-one hydrochloride (compound B1) is dissolved in 1000 ml of DCM and 130 ml triethylamine and cooled in an icebath. A solution of 75 g chloroacetic anhydride in 200 ml of DCM is added, the icebath removed and the mixture is stirred at RT until the starting material is consumed (60 min). The reaction mixture is washed with 400 ml of water, 200 ml of 1 M $Na_2CO_3$ (twice), dried over $MgSO_4$ and concentrated in vacuo. The title compound is purified by filtering over silica in EA and crystallized from diethyl ether.

M.p. 146-148° C.

Alternative:

430 g 5-(3,4-dimethoxyphenyl)-4,4-dimethyl-2-piperidin-4-yl-2,4-dihydro-3H-pyrazol-3-one (compound B1; synthesis alternative 2) and 215 g potassium carbonate are suspended in 6.5 l of DCM. The mixture is heated to reflux and 162 g chloroacetylchlorid is added drop wise during 1 h. The mixture is stirred at reflux temperature for 5 h, then 30 g of potassium carbonate and further 36 g of chloroacetylchlorid are added. After 1 h additional reaction time at reflux the reaction is complete. 116 g of acetic acid is added to the mixture during 10 min, then the mixture is cooled to 20° C. and during cooling 3 l of water is added. The organic layer is separated from the aqueous layer; the organic layer is washed twice with 1.5 l of water. The combined aqueous layers are extracted twice with 0.5 l of DCM. The organic layers are combined and 6 l is distilled off in vacuum. Then 2.5 l of tert. butylmethylether is added and the solution is concentrated in vacuum until crystallization starts (about 0.8 liter is distilled off). The suspension is cooled down and stirred overnight. The suspension is filtered, the solid dried in vacuum by 50° C.

M.p. 146.5-148.5° C.

A2. 2-[1-(chloroacetyl)piperidin-4-yl]-5-(3,4-diethoxyphenyl)-4,4-dimethyl-2,4-dihydro-3H-pyrazol-3-one Prepared analogously as described for example A1 using 5-(3,4-diethoxyphenyl)-4,4-dimethyl-2-piperidin-4-yl-2,4-dihydro-3H-pyrazol-3-one hydrochloride (compound B2) and chloroacetic anhydride as starting compounds.

MS [M+H] calc: 436 found: 436

A3. 2-[1-(chloroacetyl)piperidin-4-yl]-5-[3-(cyclopropylmethoxy)-4-(difluoromethoxy)phenyl]-4,4-dimethyl-2,4-dihydro-3H-pyrazol-3-one Prepared analogously as described for example A1 using 5-[3-(cyclopropylmethoxy)-4-(difluoromethoxy)phenyl]-4,4-dimethyl-2-piperidin-4-yl-2,4-dihydro-3H-pyrazol-3-one hydrochloride (compound B3) and chloroacetic anhydride as starting compounds.

MS [M+H]: calc: 484 found: 484

A4. 1-(2-{4-[3-(3-hydroxy-4-methoxyphenyl)-4,4-dimethyl-5-oxo-4,5-dihydro-1H-pyrazol-1-yl]piperidin-1-yl}-2-oxoethyl)pyrrolidine-2,5-dione Step 3: A mixture of 5.5 g of 1-[2-(4-{3-[3-(benzyloxy)-4-methoxyphenyl]-4,4-dimethyl-5-oxo-4,5-dihydro-1H-pyrazol-1-yl}piperidin-1-yl)-2-oxoethyl]pyrrolidine-2,5-dione (see below), 0.2 g of 10% Pd/C and 3 g of ammonium formiate in 150 ml methanol is refluxed for 10 min. After cooling to RT, the mixture is filtered over Hyflo and the solution evaporated. The residue is washed with EA and dried.

M.p. 136-139° C.

Step 2: 1-[2-(4-{3-[3-(benzyloxy)-4-methoxyphenyl]-4,4-dimethyl-5-oxo-4,5-dihydro-1H-pyrazol-1-yl}-piperidin-1-yl)-2-oxoethyl]pyrrolidine-2,5-dione Prepared analogously as described for example 1 using 5-[3-(benzyloxy)-4-methoxyphenyl]-2-[1-(chloroacetyl)piperidin-4-yl]-4,4-dimethyl-2,4-dihydro-3H-pyrazol-3-one (see below) and succinimide as starting compounds.

M.p. 212-214° C.

Step 1: 5-[3-(benzyloxy)-4-methoxyphenyl]-2-[1-(chloroacetyl)piperidin-4-yl]-4,4-dimethyl-2,4-dihydro-3H-pyrazol-3-one Prepared analogously as described for example A1 using 5-[3-(benzyloxy)-4-methoxyphenyl]-4,4-dimethyl-2-piperidin-4-yl-2,4-dihydro-3H-pyrazol-3-one hydrochloride (compound B4) and chloroacetic anhydride as starting compounds.

M.p. 93-97° C.

A5. 2-[1-(chloroacetyl)piperidin-4-yl]-5-(7-methoxy-2,2-dimethyl-2,3-dihydro-1-benzofuran-4-yl)-4,4-dimethyl-2,4-dihydro-3H-pyrazol-3-one Prepared analogously as described for example A1 using 5-(7-methoxy-2,2-dimethyl-2,3-dihydro-1-benzofuran-4-yl)-4,4-dimethyl-2-piperidin-4-yl-2,4-dihydro-3H-pyrazol-3-one hydrochloride (compound B5) and chloroacetic anhydride as starting compounds.

M.p. 205-207° C.

A6. 2-[1-(chloroacetyl)piperidin-4-yl]-5-(7-methoxy-3H-spiro[1-benzofuran-2,1-cyclopentan]-4-yl)-4,4-dimethyl-2,4-dihydro-3H-pyrazol-3-one Prepared analogously as described for example A1 using 5-(7-methoxy-3H-spiro[1-benzofuran-2,1'-cyclopentan]-4-yl)-4,4-dimethyl-2-piperidin-4-yl-2,4-dihydro-3H-pyrazol-3-one hydrochloride (compound B6) and chloroacetic anhydride as starting compounds.

M.p. 208-213° C.

A7. 2-[1-(chloroacetyl)piperidin-4-yl]-5-(3,4-dimethoxyphenyl)-4,4-diethyl-2,4-dihydro-3H-pyrazol-3-one Title compound may be prepared analogously as described for example A1 using 5-(3,4-dimethoxyphenyl)-4,4-diethyl-2-piperidin-4-yl-2,4-dihydro-3H-pyrazol-3-one hydrochloride (compound B7) and chloroacetic anhydride as starting compounds.

A8. 2-[1-(chloroacetyl)piperidin-4-yl]-5-(3,4-dimethoxyphenyl)-4-methyl-4-propyl-2,4-dihydro-3H-pyrazol-3-one Prepared analogously as described for A1 using 5-(3,4-dimethoxyphenyl)-4-methyl-2-piperidin-4-yl-4-propyl-2,4-dihydro-3H-pyrazol-3-one hydrochloride (compound B8) and chloroacetic anhydride as starting compounds.

MS [M+H] calc: 436 found: 436

A9. 2-[1-(chloroacetyl)piperidin-4-yl]-5-(3,4-dimethoxyphenyl)-4-ethyl-4-methyl-2,4-dihydro-3H-pyrazol-3-one Prepared analogously as described for A1 using 5-(3,4-dimethoxyphenyl)-4-ethyl-4-methyl-2-piperidin-4-yl-2,4-dihydro-3H-pyrazol-3-one hydrochloride (compound B9) and chloroacetic anhydride as starting compounds.
MS [M+H] calc: 422 found: 422

A10. 2-[1-(chloroacetyl)piperidin-4-yl]-4-(3,4-dimethoxyphenyl)-2,3-diazaspiro[4.4]non-3-en-1-one Prepared analogously as described for A1 using 4-(3,4-dimethoxyphenyl)-2-piperidin-4-yl-2,3-diazaspiro[4.4]non-3-en-1-one hydrochloride (compound B10) and chloroacetic anhydride as starting compounds.
MS [M+H] calc: 434 found: 434

B1. 5-(3,4-dimethoxyphenyl)-4,4-dimethyl-2-piperidin-4-yl-2,4-dihydro-3H-pyrazol-3-one hydrochloride Alternative 1: Preparation of the title compound starting from compound C1:

20 g NaH (60% in mineral oil) is suspended in 500 ml of dry DMF under a blanket of dry nitrogen. 124 g 5-(3,4-dimethoxyphenyl)-4,4-dimethyl-2,4-dihydro-3H-pyrazol-3-one (compound C1) is added in portions and stirred for an additional 30 min at RT. The solution becomes slightly yellow. 168 g tert-butyl 4-(Toluene-4-sulfonyloxy)-piperidine-1-carboxylate (compound E1) in 150 ml of DMF is added in one portion and the mixture is placed in a preheated oil bath (140° C.) and heated for 1.0 hr. The mixture is cooled to 50° C. (part of the sodium toluenesulfonate crystallizes) 1000 ml of water is added and the mixture is extracted with 200 ml of ethyl acetate (five times). The combined organic layers are washed with 100 ml of water (five times), 50 ml of brine, dried over $MgSO_4$ and concentrated in vacuo. The oil obtained is dissolved in 300 ml of ethanol and 300 ml of 1M $H_2SO_4$ is added and heated at reflux for 60 min. The ethanol is removed in vacuo, 200 ml of water is added and washed with 100 ml DCM (five times). The aqueous layer is basified with 40 g NaOH in 250 ml water and extracted with 200 ml of dichloromethane (three times), dried over $MgSO_4$ and concentrated in vacuo. The oil is suspended in 300 ml of ethanol with 30 ml of concentrated hydrochloric acid and heated until it dissolves. Cooling in ice causes precipitation.
M.p. 217-220° C.

Alternative 2: Preparation of 5-(3,4-dimethoxyphenyl)-4,4-dimethyl-2-piperidin-4-yl-2,4-dihydro-3H-pyrazol-3-one starting from compound D1:

1000 g of methyl 3-(3,4-dimethoxyphenyl)-2,2-dimethyl-3-oxopropanoate (compound D1) are dissolved in 10.5 l of methanol. 2500 g piperidin-4-yl-hydrazine-dihydrochloride, solved in 4 l of water are added rapidly. The mixture is heated to reflux and kept at reflux temperature for 4 days. The reaction mixture is cooled to 20° C., 10 l of water are added and then methanol is removed by distillation in vacuum. The aqueous solution is allowed to stand overnight at RT. The solution is cooled and aqueous sodium hydroxide (c=10 mol/l) (about 2 l) is added during 4 to 5 h by keeping the temperature below 20° C. and the pH should be higher than 13. The product crystallizes during adding of sodium hydroxyide. The mixture is stirred 1 h at 10° C., filtered over a filter press and washed with 0.5 l of water. The product is dried at 50° C. in a circulating air dryer.
M.p. 119-122° C.

B2. 5-(3,4-diethoxyphenyl)-4,4-dimethyl-2-piperidin-4-yl-2,4-dihydro-3H-pyrazol-3-one hydrochloride Prepared analogously as described for example B1 (Alternative 1) using 5-(3,4-diethoxyphenyl)-4,4-dimethyl-2,4-dihydro-3H-pyrazol-3-one (compound C2) and tert-butyl 4-(Toluene-4-sulfonyloxy)-piperidine-1-carboxylate (compound E1) as starting compounds.
M.p. 221-224° C.

B3. 5-[3-(cyclopropylmethoxy)-4-(difluoromethoxy)phenyl]-4,4-dimethyl-2-piperidin-4-yl-2,4-dihydro-3H-pyrazol-3-one hydrochloride Prepared analogously as described for example B1 (Alternative 1) using 5-[3-(cyclopropylmethoxy)-4-(difluoromethoxy)phenyl]-4,4-dimethyl-2,4-dihydro-3H-pyrazol-3-one (compound C3) and tent-butyl 4-(Toluene-4-sulfonyloxy)-piperidine-1-carboxylate (compound E1) as starting compounds.
M.p. 236-237° C.

B4. 5-[3-(benzyloxy)-4-methoxyphenyl]-4,4-dimethyl-2-piperidin-4-O-2,4-dihydro-3H-pyrazol-3-one hydrochloride Prepared analogously as described for example B1 (Alternative 1) using 5-[3-(benzyloxy)-4-methoxyphenyl]-4,4-dimethyl-2,4-dihydro-3H-pyrazol-3-one (compound C4) and tert-butyl 4-(Toluene-4-sulfonyloxy)-piperidine-1-carboxylate (compound E1) as starting compounds.
M.p. 243° C. (with decomposition)

B5. 5-(7-methoxy-2,2-dimethyl-2,3-dihydro-1-benzofuran-4-yl)-4,4-dimethyl-2-piperidin-4-yl-2,4-dihydro-3H-pyrazol-3-one hydrochloride Prepared analogously as described for example B1 (Alternative 1) using 5-(7-methoxy-2,2-dimethyl-2,3-dihydro-1-benzofuran-4-yl)-4,4-dimethyl-2,4-dihydro-3H-pyrazol-3-one (compound C5) and fedbutyl 4-(Toluene-4-sulfonyloxy)-piperidine-1-carboxylate (compound E1) as starting compounds.
M.p.>260° C.

B6. 5-(7-methoxy-3H-spiro[1-benzofuran-2,1'-cyclopentan]-4-yl)-4,4-dimethyl-2-piperidin-4-yl-2,4-dihydro-3H-pyrazol-3-one hydrochloride Prepared analogously as described for example B1 (Alternative 1) using 5-(7-methoxy-3H-spiro[1-benzofuran-2,1-cyclopentan]-4-yl)-4,4-dimethyl-2,4-dihydro-3H-pyrazol-3-one (compound C6) and tert-butyl 4-(Toluene-4-sulfonyloxy)-piperidine-1-carboxylate (compound E1) as starting compounds.
M.p. 212° C. (with decomposition)

B7. 5-(3,4-dimethoxyphenyl)-4,4-diethyl-2-piperidin-4-yl-2,4-dihydro-3H-pyrazol-3-one hydrochloride The title compound may be prepared analogously as described for B1 (Alternative 1) using 5-(3,4-dimethoxyphenyl)-4,4-diethyl-2,4-dihydro-3H-pyrazol-3-one (compound C7) and tert-butyl 4-(Toluene-4-sulfonyloxy)-piperidine-1-carboxylate (compound E1) as starting compounds.

B8. 5-(3,4-dimethoxyphenyl)-4-methyl-2-piperidin-4-yl-4-propyl-2,4-dihydro-3H-pyrazol-3-one hydrochloride Prepared analogously as described for example B1 (Alternative 1) using 5-(3,4-dimethoxyphenyl)-4-methyl-4-propyl-2,4-dihydro-3H-pyrazol-3-one (compound C8) and Cert-butyl 4-(Toluene-4-sulfonyloxy)-piperidine-1-carboxylate (compound E1) as starting compounds.
M.p. 147-152° C.

B9. 5-(3,4-dimethoxyphenyl)-4-ethyl-4-methyl-2-piperidin-4-yl-2,4-dihydro-3H-pyrazol-3-one hydrochloride Prepared analogous as described for example B1 (Alternative 1) using 5-(3,4-dimethoxyphenyl)-4-ethyl-4-methyl-2,4-dihydro-3H-pyrazol-3-one (compound C9) and tert-butyl 4-(Toluene-4-sulfonyloxy)piperidine-1-carboxylate (compound E1) as starting compounds.
M.p. 214-216° C.

B10. 4-(3,4-dimethoxyphenyl)-2-piperidin-4-yl-2,3-diazaspiro[4.4]non-3-en-1-one hydrochloride Prepared analogous as described for example B1 (Alternative 1) using 4-(3,4-dimethoxyphenyl)-2,3-diazaspiro[4.4]non-3-en-1-one (compound C10) and tert-butyl 4-(Toluene-4-sulfonyloxy)-piperidine-1-carboxylate (compound E1) as starting compounds.
M.p. 235° C. (with decomposition)

C1. 5-(3,4-dimethoxyphenyl)-4,4-dimethyl-2,4-dihydro-3H-pyrazol-3-one 192 g of methyl 3-(3,4-dimethoxyphenyl)-2,2-dimethyl-3-oxopropanoate (compound D1) is dissolved in 600 ml of ethanol 145 ml hydrazine hydrate is added and the mixture is heated under reflux for 17 h. The mixture is concentrated in vacuo, resuspended in 400 ml of ethanol and concentrated again. The solids are refluxed for 60 min in 400 ml of ethanol, cooled to RT and filtered. The product is washed with 50 ml of ethanol followed by 100 ml of diethyl ether and dried in vacuo at 50° C.
M.p. 193-194° C.

C2. 5-(3,4-diethoxyphenyl)-4,4-dimethyl-2,4-dihydro-3H-pyrazol-3-one

Prepared analogously as described for example C1 using methyl 3-(3,4-diethoxyphenyl)-2,2-dimethyl-3-oxopropanoate (compound D2) and hydrazine hydrate as starting compounds.
M.p. 121-122° C.

C3. 5-[3-(cyclopropylmethoxy)-4-(difluoromethoxy)phenyl]-4,4-dimethyl-2,4-dihydro-3H-pyrazol-3-one Prepared analogously as described for example C1 using methyl 3-[3-(cyclopropylmethoxy)-4-(difluoromethoxy)phenyl]-2,2-dimethyl-3-oxopropanoate (compound D3) and hydrazine hydrate as starting compounds.
M.p. 83-85° C.

C4. 5-[3-(benzyloxy)-4-methoxyphenyl]-4,4-dimethyl-2,4-dihydro-3H-pyrazol-3-one Prepared analogously as described for example C1 using methyl 3-[3-(benzyloxy)-4-methoxyphenyl]-2,2-dimethyl-3-oxopropanoate (compound D4) and hydrazine hydrate as starting compounds.
M.p. 201-206° C.

C5. 5-(7-methoxy-2,2-dimethyl-2,3-dihydro-1-benzofuran-4-yl)-4,4-dimethyl-2,4-dihydro-3H-pyrazol-3-one 1.1 g of diisopropylamine is dissolved in 50 ml of THF under a blanket of dry nitrogen and cooled to 0° C. and 7.5 ml n-BuLi (1.6M in hexane) is added dropwise. Next, the mixture is cooled to minus 40° C., using an acetone/N2 bath, and 1.2 g of methyl 2-methylproponate is added. The resulting mixture is stirred for an additional 15 min at minus 40° C., after which 2.6 g of 7-methoxy-2,2-dimethyl-2,3-dihydrobenzofuran-4-carbonyl chloride dissolved in 50 ml of THF is added dropwise in 60 min during which the temperature is kept below −40° C. The cooling bath is removed and stirring is continued for 60 min at RT. 10 ml of 4M hydrochloric acid is added, the THF is removed in vacuo and the aqueous layer is extracted with ethyl acetate. The ethyl acetate solution is washed subsequently with 50 ml of water, 50 ml 1M sodium carbonate and 50 ml of brine, dried over $MgSO_4$ and concentrated in vacuo. The residue is dissolved in ethanol, 2.4 g of hydrazine hydrate is added and the resulting mixture refluxed for 18 h. After cooling to room temperature, the precipitate is filtered off and dried.
M.p. 202-205° C.

C6. 5-(7-methoxy-3H-spiro[1-benzofuran-2,1'-cyclopentan]-4-yl)-4,4-dimethyl-2,4-dihydro-3H-pyrazol-3-one Prepared analogous as described for example C5 using 7-methoxy-2,2-spirocyclopentyl-2,3-dihydrobenzofuran-4-carbonyl chloride, methyl 2-methylproponate and hydrazine hydrate as starting compounds.
M.p. 214-215° C.

C7. 5-(3,4-dimethoxyphenyl)-4,4-diethyl-2,4-dihydro-3H-pyrazol-3-one

The title compound may be prepared analogously as described for example C5 using 3,4-dimethoxybenzoyl chloride, methyl 2-ethylbutanoate and hydrazine hydrate as starting compounds.

C8. 5-(3,4-dimethoxyphenyl)-4-methyl-4-propyl-2,4-dihydro-3H-pyrazol-3-one

Prepared analogously as described for example C5 using 3,4-dimethoxybenzoyl chloride, methyl 2-methylpentanoate and hydrazine hydrate as starting compounds.
M.p. 119-120° C.

C9. 5-(3,4-dimethoxyphenyl)-4-ethyl-4-methyl-2,4-dihydro-3H-pyrazol-3-one

Prepared analogously as described for example C5 using 3,4-dimethoxybenzoyl chloride, methyl 2-methylbutanoate and hydrazine hydrate as starting compounds.
M.p. 145-146° C.

C10. 4-(3,4-dimethoxyphenyl)-2,3-diazaspiro[4.4] non-3-en-1-one

Prepared analogously as described for example C5 using 3,4-dimethoxybenzoyl chloride, methyl cyclopentancarboxylate and hydrazine hydrate as starting compounds.
M.p. 200-202° C.

D1. Methyl 3-(3,4-dimethoxyphenyl)-2,2-dimethyl-3-oxopropanoate 124 ml of diisopropylamine is dissolved in 500 ml of THF under a blanket of dry nitrogen and cooled to 0° C. and 550 ml n-BuLi (1.6M in hexane) is added dropwise. Next, the mixture is cooled to minus 40° C., using an acetone/N2 bath, and 100 ml methyl 2-methylproponate is added. The resulting mixture is stirred for an additional 15 min at minus 40° C., after which 160.5 g of 3,4-dimethoxybenzoyl chloride dissolved in 750 ml of THF is added dropwise in 60 min during which the temperature is kept below −40° C. The cooling bath is removed and stirring is continued for 60 min at RT. 150 ml of 4M hydrochloric acid is added and the THF layer is separated and washed with 100 ml of water, 200 ml 1M of sodium carbonate and 100 ml of brine, dried over $MgSO_4$ and concentrated in vacuo.
NMR ($CDCl_3$): δ=1.56 (s, 6H), 3.65 (s, 3H), 3.89 (s, 3H), 3.91 (s, 3H), 6.82 (d, J=8.4 Hz, 1H), 7.41 (dd, 1H, J=1.4, 8.4 Hz) 7.99 (d, 1H, J=1.4 Hz).

D2. Methyl 3-(3,4-diethoxyphenyl)-2,2-dimethyl-3-oxopropanoate

Prepared analogously as described for example D1 using methyl 2-methylproponate and 3,4-diethoxybenzoyl chloride as starting compounds.
NMR ($CDCl_3$): δ=1.31-154 (dt, 6H, J=5.6 Hz), 1.56 (s, 6H), 3.65 (s, 3H), 4.07 (m, 6H), 6.82 (d, J=8.4 Hz, 1H), 7.41 (dd, 1H, J=1.4, 8.4 Hz) 7.99 (d, 1H, J=1.4 Hz).

D3. Methyl 3-[3-(cyclopropylmethoxy)-4-(difluoronnethoxy)phenyl]-2,2-dimethyl-3-oxopropanoate Prepared analogously as described for example D1 using methyl 2-methylproponate and 3-cyclopropylmethoxy-4-difluoromethoxybenzoyl chloride as starting compounds.
NMR ($CDCl_3$): δ=1.20-1.33 (m, 2H), 1.50-1.63 (m, 6H), 1.46 (s, 6H), 3.65 (s, 3H), 3.57 (s, 3H), 3.82 (d, J=5.7 Hz, 2H), 6.30 (s, 0.4H), 6.68 (s, 0.6H), 7.07 (d, J=8.4 Hz, 1H), 7.27 (dd, 1H, J=1.4, 8.4 Hz), 7.49 (d, 1H, J=1.4 Hz).

D4. Methyl 3-[3-(benzyloxy)-4-methoxyphenyl]-2,2-dimethyl-3-oxopropanoate

Prepared analogously as described for example D1 using methyl 2-methylproponate and 3-benzyloxy-4-methoxybenzoyl chloride as starting compounds.
NMR ($CDCl_3$): 1.46 (s, 6H), 3.60 (s, 3H), 3.92 (s, 3H), 5.12 (2,2H), 6.83 (d, J=8.4 Hz, 1H), 7.20-7.55 (m, 7H)

E1. tert-Butyl 4-(toluene-4-sulfonyloxy)-piperidide-1-carboxylate 201 g tert Butyl 4-hydroxy-piperidine-1-carboxylate, 160 ml triethylamine and 6.0 g 4-dimethylaminopyridine are dissolved in 750 ml DCM. 191 g 4-toluenesulfonylchloride is added and the mixture is refluxed for 7 h. The mixture is cooled in ice and acidified with 100 ml of 1M $H_2SO_4$; the organic layer is washed with 300 ml of water (twice), 250 ml of 1 M $Na_2CO_3$ solution (twice), dried over $MgSO_4$, filtered and concentrated in vacuo.
M.p. 98-101° C.

F1. 5-(3,4-dimethoxyphenyl)-2-(1-glycylpiperidin-4-yl)-4,4-dimethyl-2,4-dihydro-3H-pyrazol-3-one hydrochloride Step 2: A solution of 4 g tert-Butyl (2-{4-[3-(3,4-dimethoxyphenyl)-4,4-dimethyl-5-oxo-4,5-dihydro-1H-pyrazol-1-yl]piperidin-1-yl}-2-oxoethyl)carbamate (see below) and 7 ml of trifluoroacetic acid in 50 ml of dichloromethane is stirred at RT for 16 h after which the mixture is washed with aqueous sodium carbonate. After drying over magnesium sulphate, a solution of hydrochloric acid in ether is added. The precipitate is filtered off and dried.
M.p. 70-74° C.

Step 1: tert-Butyl (2-{4-[3-(3,4-dinnethoxyphenyl)-4,4-dimethyl-5-oxo-4,5-dihydro-1H-pyrazol-1-yl]piperidin-1-yl}-2-oxoethyl)carbamate: A mixture of 5 g of 5-(3,4-dimethoxyphenyl)-4,4-dimethyl-2-piperidin-4-yl-2,4-dihydro-3H-pyrazol-3-one hydrochloride (compound B1), 1.9 ml of triethylamine and 2.5 g of N—BOC-glycine in 25 ml of DCM is stirred until complete dissolution (about 15 min). 3.9 g of 1-(3-dimethylaminopropyl)-3-ethylcarbodiimide hydrochloride is added and the resulting mixture is stirred at RT for 3 h. After washing with 1 M sodium carbonate, the organic layer is dried over magnesium sulphate and evaporated. The residue is purified by column chromatography [silica, ethyl acetate]. The title compound is crystallized from diethyl ether.
M.p. 146-148° C.

Commercial Utility

The compounds of formula 1 and the stereoisomers of the compounds of formula 1 according to the invention are hereinafter referred to as the compounds of the invention. In particular, the compounds of the invention are pharmaceutically acceptable.

The compounds of the invention have valuable pharmaceutical properties, which make them commercially utilizable. In particular, as type 4 phosphodiesterase (PDE4) inhibitors, they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways, of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds of the invention are distinguished by valuable and desirable properties, such as, for example, high efficacy, high selectivity, low toxicity, superior bioavailability in general (e.g. good enteral absorption), superior therapeutic window, superior pharmacokinetics (e.g. half life), absence of significant side effects, and further beneficial effects related to their therapeutic and pharmaceutical suitability.

Accordingly, the invention further relates to the compounds of the invention for use in the treatment or prophylaxis of diseases, especially diseases alleviated by inhibition of type 4 phosphodiesterase.

In particular, the invention relates to the compounds of the invention for use in the treatment or prophylaxis of the following diseases:

acute and chronic airway diseases, such as, but not limited to, bronchitis, allergic bronchitis, bronchial asthma, emphysema, COPD (chronic obstructive pulmonary disease), pulmonary hypertension and lung fibrosis;

diseases which are based on allergic and/or chronic, immunological false reactions in the region of the upper airways (pharynx, nose) and the adjacent regions (paranasal sinuses, eyes), such as, but not limited to, allergic rhinitis/sinusitis, chronic rhinitis/sinusitis, allergic conjunctivitis and also nasal polyps; dermatological diseases especially of proliferative, inflammatory and allergic type, such as, but not limited to psoriasis (vulgaris), toxic and allergic contact eczema, atopic dermatitis (eczema), seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea and other proliferative, inflammatory and allergic skin disorders;

diseases which are based on an excessive release of TNF and leukotrienes, such as, for example, diseases of the arthritis type like rheumatoid arthritis, rheumatoid spondylitis, osteoarthritis and other arthritic conditions;

fibrotic diseases, such as, but not limited to, cystic fibrosis, pulmonary fibrosis, hepatic fibrosis and renal fibrosis;

viral, alcoholic or drug-induced acute and fulminant hepatitis, hepatic steatosis (alcoholic and non-alcoholic steatiohepatitis);

diseases of the immune system, such as, but not limited to, AIDS, multiple sclerosis, graft versus host reaction, allograft rejections;

cachexia, cancer cachexia, AIDS cachexia;

types of shock, such as, but not limited to, septic shock, endotoxin shock, gram-negative sepsis, toxic shock syndrome and ARDS (adult respiratory distress syndrome);

diseases in the gastrointestinal region, such as Crohn's disease and ulcerative colitis;

diseases of the heart which can be treated by PDE inhibitors, such as cardiac insufficiency;

diseases which can be treated on account of the tissue-relaxant action of the PDE inhibitors, such as, for example, erectile dysfunction, colics of the kidneys and of the ureters in connection with kidney stones or oncolytic action (to treat preterm delivery); glomerulonephritis;

diabetes insipidus, diabetes mellitus (type I and in particular type II); cancer (in particular lymphoid and myeloid leukaemia); osteoporosis;

conditions associated with cerebral metabolic inhibition, such as, but not limited to, cerebral senility, senile dementia (Alzheimer's disease), memory impairment associated with Parkinson's disease or multiinfarct dementia;

and also diseases of the central nervous system, such as, but not limited to, depressions, anxiety states, spinal cord injury, schizophrenia or arteriosclerotic dementia.

Preferably, the invention further relates to the compounds of the invention for use in the treatment or prophylaxis of the following diseases:

acute and chronic airway diseases, such as bronchitis, allergic bronchitis, bronchial asthma, emphysema, COPD, pulmonary hypertension and lung fibrosis;

allergic rhinitis;

rheumatoid arthritis;

dermatological diseases, such as psoriasis and atopic dermatitis (eczema);

inflammations in the gastrointestinal region, such as Crohn's disease and ulcerative colitis and diabetes mellitus (type I and in particular type II).

The invention also relates to the use of a compound of the invention in the manufacture of a pharmaceutical composition inhibiting the type 4 phosphodiesterase, in particular a pharmaceutical composition for the treatment or prophylaxis of diseases alleviated by inhibition of type 4 phosphodiesterase, preferably, a pharmaceutical composition for the treatment or prophylaxis of the diseases exemplified above.

In particular, the invention relates to the use of a compound of the invention in the manufacture of a pharmaceutical composition for the treatment or prophylaxis of an acute or chronic airway disease, such as, but not limited to, bronchitis, allergic bronchitis, bronchial asthma, emphysema, COPD, pulmonary hypertension or lung fibrosis.

The invention relates also to the use of a compound of the invention in the manufacture of a pharmaceutical composition for the treatment or prophylaxis of allergic rhinitis.

Furthermore, the invention relates to the use of a compound of the invention in the manufacture of a pharmaceutical composition for the treatment or prophylaxis of dermatological diseases, such as, but not limited to, psoriasis or atopic dermatitis (eczema).

Additionally, the invention relates to the use of a compound of the invention in the manufacture of a pharmaceutical composition for the treatment or prophylaxis of inflammations in the gastrointestinal region, such as, but not limited to, Crohn's disease or ulcerative colitis.

As well, the invention relates to the use of a compound of the invention in the manufacture of a pharmaceutical composition for the treatment or prophylaxis of diabetes mellitus (type I and in particular type II).

The invention further relates to a method of treating or preventing a disease comprising administering to a patient in need thereof a therapeutically effective amount of at least one of the compounds of the invention.

In particular, the invention relates to a method of treating or preventing one of the above mentioned diseases comprising administering to a patient in need thereof a therapeutically effective amount of at least one of the compounds of the invention.

Especially, the invention relates to a method of treating or preventing a disease, which is alleviated by inhibition of the type 4 phosphodiesterase comprising administering to a patient in need thereof a therapeutically effective amount of at least one of the compounds of the invention.

Preferably, the invention relates to a method of treating or preventing an acute or chronic airway disease, for example, but not limited to, bronchitis, allergic bronchitis, bronchial asthma, emphysema, COPD, pulmonary hypertension or lung fibrosis comprising administering to a patient in need thereof a therapeutically effective amount of at least one of the compounds of the invention.

The invention relates also to a method of treating or preventing allergic rhinitis comprising administering to a patient in need thereof a therapeutically effective amount of at least one of the compounds of the invention.

Furthermore, the invention preferably relates to a method of treating or preventing dermatological diseases, such as, but not limited to, psoriasis or atopic dermatitis (eczema) comprising administering to a patient in need thereof a therapeutically effective amount of at least one of the compounds of the invention.

Additionally, the invention preferably relates to a method of treating or preventing diseases in the gastrointestinal region, such as, but not limited to, Crohn's disease or ulcerative colitis comprising administering to a patient in need thereof a therapeutically effective amount of at least one of the compounds of the invention.

As well, the invention preferably relates to a method of treating or preventing diabetes mellitus (type I and in particular type II) comprising administering to a patient in need thereof a therapeutically effective amount of at least one of the compounds of the invention.

In the above methods, the patient is preferably a mammal, more preferably a human. Furthermore, in the above methods, at least one of the compounds of the invention can be used. Preferably, one or two of the compounds of the invention are used, more preferably, one of the compounds of the invention is used.

In a particularly preferred embodiment of the invention, the above methods of treating or preventing one of the above mentioned diseases comprise administering to a patient in need thereof a therapeutically effective amount of one compound of the examples according to the present invention.

The invention furthermore relates to a pharmaceutical composition, which comprises at least one of the compounds of the invention together with at least one pharmaceutically acceptable auxiliary.

Preferably, the pharmaceutical composition comprises one or two of the compounds of the invention. More preferably, the pharmaceutical composition comprises one of the compounds of the invention.

In a particularly preferred embodiment of the invention, the pharmaceutical composition comprises a compound of the examples according to the present invention together with at least one pharmaceutically acceptable auxiliary.

The invention furthermore relates to a pharmaceutical composition according to the invention inhibiting the type 4 phosphodiesterase, especially for the treatment or prophylaxis of diseases alleviated by inhibition of type 4 phosphodiesterase, in particular for the treatment or prophylaxis of the diseases exemplified above.

The invention also encompasses pharmaceutical compositions according to the invention, as defined above, for the treatment or prophylaxis of one or more of the following diseases: acute and chronic airway diseases, such as, bronchitis, allergic bronchitis, bronchial asthma, emphysema, COPD, pulmonary hypertension and lung fibrosis; allergic rhinitis; rheumatoid arthritis; dermatological diseases, such as psoriasis and atopic dermatitis (eczema); and inflammations in the gastrointestinal region, such as Crohn's disease and ulcerative colitis; and diabetes mellitus (type I and in particular type II)

Depending on the particular disease to be treated or prevented, additionally therapeutic agents, which are normally administered to treat or prevent that disease, may optionally be co-administered with the compounds of the invention.

In a preferred embodiment, at least one of the compounds of the invention is co-administered with at least one therapeutic agent selected from the group consisting of corticosteroids, anticholinergics, $\beta_2$-adrenoceptor agonists, H1 receptor antagonists, leukotriene receptor antagonists, type 5 phosphodiesterase inhibitors, HMG-CoA reductase-inhibitors, lung surfactants, antibiotics and anti-diabetic agents.

In this respect, the "therapeutic agent" includes the corticosteroids, anticholinergics, ($\beta_2$-adrenoceptor agonists, H1 receptor antagonists, leukotriene receptor antagonists, type 5 phosphodiesterase inhibitors, HMG-CoA reductase-inhibitors, lung surfactants, antibiotics and anti-diabetics in form of the free compounds, the pharmaceutically acceptable salts thereof, the pharmaceutically acceptable derivetives thereof (e.g., but not limited to, ester derivatives, N-oxides etc.), the solvates (hydrates) thereof and the stereoisomers of the compounds, salts, derivatives and solvates.

Co-administration of at least one of the compounds of the invention with at least one therapeutic agent selected from the group consisting of corticosteroids, anticholinergics, $\beta_2$-adrenoceptor agonists, H1 receptor antagonists, leukotriene receptor antagonists, type 5 phosphodiesterase inhibitors, HMG-CoA reductase-inhibitors, lung surfactants, antibiotics and anti-diabetic agents can take place in form of a fixed combination, a non-fixed combination or a kit of parts.

A "fixed combination" is defined as a combination wherein the compound of the invention and the therapeutic agent intended for co-administration are present in one dosing unit or in a single entity. One example of a fixed combination is a pharmaceutical composition wherein the compound of the invention and the therapeutic agent are present in admixture for simultaneous administration. Another example of a fixed combination is a pharmaceutical composition wherein the compound of the invention and the therapeutic compound are present in one dosing unit without being in admixture.

A "non-fixed combination" or "kit of parts" is defined as a combination wherein the compound of the invention and the therapeutic agent are present in more than one dosing unit. In a non-fixed combination or a kit of parts the compound of the invention and the therapeutic compound are provided as separate formulations. They might be packaged and presented together as separate components of a combination pack for simultaneous, sequential or separate use in combination therapy. In case of sequential or separate administration of the compound of the invention and the therapeutic agent, the compound of the invention can be administered before or after administration of the therapeutic agent.

The type of formulation of the compound of the invention and the therapeutic agent of a non-fixed combination or a kit of parts can be identical, similar, i.e. both, the compound of the invention and the therapeutic agent are formulated in separate tablets or capsules, or can be different, i.e. suited for different administration forms, such as e.g. the compound of the invention is formulated as tablet or capsule and the therapeutic agent is formulated as powder, solution or suspension.

Accordingly, the invention additionally relates to a fixed combination, a non-fixed combination or kit of parts comprising at least one of the compounds of the invention, at least one therapeutic agent selected from the group consisting of corticosteroids, anticholinergics, $\beta_2$-adrenoceptor agonists, H1 receptor antagonists, leukotriene receptor antagonists, type 5 phosphodiesterase inhibitors, HMG-CoA reducetase-inhibitors, lung surfactants, antibiotics and anti-diabetic agents, and at least one pharmaceutically acceptable auxiliary.

The above-mentioned combinations of a compound of the invention and a therapeutic agent selected from the group consisting of corticosteroids, anticholinergics, $\beta_2$-adrenoceptor agonists, H1 receptor antagonists, leukotriene receptor antagonists, type 5 phosphodiesterase inhibitors, HMG-CoA reductase-inhibitors, lung surfactants and antibiotics are particularly useful for the treatment of acute and chronic airway diseases. Combinations of a compound of the invention and a therapeutic agent selected from the group consisting of corticosteroids, H1 receptor antagonists and leukotriene receptor antagonists might as well be useful for the systemic or topical treatment of dermatogical diseases. Combinations of a compound of the invention and an anti-diabetic agent are useful for the treatment of diabetes mellitus (type I and in particular type II).

In a preferred embodiment, the above-mentioned fixed combination, non-fixed combination or kit of parts comprise a compound of the invention (in particular the compound of the invention is one of the examples of the invention), a corticosteroid and at least one pharmaceutically acceptable auxiliary. In a particularly preferred embodiment, the above-mentioned fixed combination, non-fixed combination or kit of parts comprise:
a compound of the invention and budesonide,
a compound of the invention and fluticasone,
a compound of the invention and beclometasone,
a compound of the invention and mometasone,
a compound of the invention and triamcinolone acetonide, or
a compound of the invention and ciclesonide,
and at least one pharmaceutically acceptable auxiliary.

In a preferred embodiment, the pharmaceutically acceptable salt of fluticasone is fluticasone-17-propionate. In another preferred embodiment, the pharmaceutically acceptable salt of beclometasone is beclometasone dipropionate. In a preferred embodiment, the pharmaceutically acceptable salt of mometasone is mometasone furoate.

In a preferred embodiment, the above-mentioned fixed combination, non-fixed combination or kit of parts comprise a compound of the invention (in particular the compound of the invention is one of the examples of the invention), an anticholinergic and at least one pharmaceutically acceptable auxiliary. In a particularly preferred embodiment, the above-mentioned fixed combination, non-fixed combination or kit of parts comprise:
a compound of the invention and glycopyrronium bromide,
a compound of the invention and aclidinium bromide,
a compound of the invention and tiotropium bromide, or
a compound of the invention and ipratropium bromide,
and at least one pharmaceutically acceptable auxiliary.

In a preferred embodiment, the stereoisomer of glycopyrronium bromide is (R,R)-glycopyrronium bromide. In a preferred embodiment, tiotropium bromide is used in form of its monohydrate.

In a preferred embodiment, the above-mentioned fixed combination, non-fixed combination or kit of parts comprise a compound of the invention (in particular the compound of the invention is one of the examples of the invention), a $\beta_2$-adrenoceptor agonist and at least one pharmaceutically acceptable auxiliary. In a particularly preferred embodiment, the above-mentioned fixed combination, non-fixed combination or kit of parts comprise:
a compound of the invention and salbutamol,
a compound of the invention and milveterol,
a compound of the invention and indacaterol,
a compound of the invention and carmoterol,
a compound of the invention and salmeterol, or
a compound of the invention and formoterol,
and at least one pharmaceutically acceptable auxiliary.

In a preferred embodiment, the pharmaceutically acceptable salt of salbutamol is salbutamol sulfate. In a preferred embodiment, the pharmaceutically acceptable salt of milveterol is milveterol hydrochloride. In a preferred embodiment, the pharmaceutically acceptable salt of carmoterol is carmoterol hydrochloride. In a preferred embodiment, the pharmaceutically acceptable salt of salmeterol is salmeterol xinafoate. In another preferred embodiment, the pharmaceutically acceptable salt of formoterol is formoterol hemifumarate monohydrate. In another preferred embodiment, the stereoisomer of formoterol is R,R-formoterol. In another preferred embodiment, the pharmaceutically acceptable salt of R,R-formoterol is R,R-formoterol L-tartrate.

In a preferred embodiment, the above-mentioned fixed combination, non-fixed combination or kit of parts comprise a compound of the invention (in particular the compound of the invention is one of the examples of the invention), a H1 receptor antagonist and at least one pharmaceutically acceptable auxiliary. In a particularly preferred embodiment, the above-mentioned fixed combination, non-fixed combination or kit of parts comprise:
a compound of the invention and azelastine,
a compound of the invention and olopatadine,
a compound of the invention and loratadine,
a compound of the invention and desloratadine, or
a compound of the invention and cetirizine,
and at least one pharmaceutically acceptable auxiliary.

In a preferred embodiment, the pharmaceutically acceptable salt of azelastine is azelastine hydrochloride. In a preferred embodiment, the pharmaceutically acceptable salt of olapatadine is olapatadine hydrochloride. In a preferred embodiment, the pharmaceutically acceptable salt of cetirizine is cetirizine dihydrochloride. In a preferred embodiment, the stereoisomer of cetirizine is levocetirizine. In another preferred embodiment, the pharmaceutically acceptable salt of levocetirizine is levocetirizine dihydrochloride.

In a preferred embodiment, the above-mentioned fixed combination, non-fixed combination or kit of parts comprise a compound of the invention (in particular the compound of the invention is one of the examples of the invention), a leukotriene receptor antagonist and at least one pharmaceutically acceptable auxiliary. In a particularly preferred embodiment, the above-mentioned fixed combination, non-fixed combination or kit of parts comprise:
a compound of the invention and montelukast,
a compound of the invention and pranlukast,
a compound of the invention and zafirlukast, or
a compound of the invention and zileuton,
and at least one pharmaceutically acceptable auxiliary.

In a preferred embodiment, the pharmaceutically acceptable salt of montelukast is montelukast sodium. In another preferred embodiment, pranlukast is used in form of its monohydrate.

In a preferred embodiment, the above-mentioned fixed combination, non-fixed combination or kit of parts comprise a compound of the invention (in particular the compound of the invention is one of the examples of the invention), a type 5 phosphodiesterase inhibitor and at least one pharmaceutically acceptable auxiliary. In a particularly preferred embodiment, the above-mentioned fixed combination, non-fixed combination or kit of parts comprise:
a compound of the invention and sildenafil,
a compound of the invention and vardenafil,
a compound of the invention and tadalafil,
a compound of the invention and udenafil, or
a compound of the invention and avanafil,
and at least one pharmaceutically acceptable auxiliary.

In another preferred embodiment, the pharmaceutically acceptable salts of sildenafil are sildenafil hemi-citrate, sildenafil citrate and sildenafil mesilate; particularly preferred is the citrate salt of sildenafil. In another preferred embodiment, the pharmaceutically acceptable salts of vardenafil are vardenafil hydrochloride or vardenafil dihydrochloride. In another preferred embodiment, the pharmaceutically acceptable salt of avanafil is avanafil besilate.

In a preferred embodiment, the above-mentioned fixed combination, non-fixed combination or kit of parts comprise a compound of the invention (in particular the compound of the invention is one of the examples of the invention), a HMG-CoA reductase inhibitor and at least one pharmaceutically acceptable auxiliary. In a particularly preferred embodiment, the above-mentioned fixed combination, non-fixed combination or kit of parts comprise:
a compound of the invention and lovastatin,
a compound of the invention and pravastatin,
a compound of the invention and simvastatin,
a compound of the invention and atorvastatin,
a compound of the invention and fluvastatin,
a compound of the invention and rosuvastatin,
a compound of the invention and pitavastatin,
a compound of the invention and bervastatin,
a compound of the invention and dalvastatin, or
a compound of the invention and glenvastatin,
and at least one pharmaceutically acceptable auxiliary.

In a preferred embodiment the pharmaceutically acceptable salts of pravastatin are the potassium, lithium, sodium and hemi-calcium salt of pravastatin. A particularly preferred pharmaceutically acceptable salt of pravastatin is the sodium salt of pravastatin. In a preferred embodiment the pharmaceutically acceptable salt of simvastatin is the sodium salt of simvastatin. In a preferred embodiment the pharmaceutically acceptable salts of atorvastatin are the potassium, sodium and the hemi-calcium salt of atorvastatin. A particularly preferred pharmaceutically acceptable salt of atorvastatin is the hemi-calcium salt of atorvastatin. As an example for a hydrate of atorvastatin may be mentioned the trihydrate and the sesquihydrate of the hemi-calcium salt of atorvastatin. In a preferred embodiment of the pharmaceutically acceptable salt of fluvastatin is the sodium salt of fluvastatin. In a preferred embodiment the pharmaceutically acceptable salts of rosuvastatin are the potassium, lithium, sodium, hemi-magnesium and the hemi-calcium salt of rosuvastatin. A particularly preferred pharmaceutically acceptable salt of rosuvastatin is the hemi-calcium salt of rosuvastatin. Another particularly preferred pharmaceutically acceptable salt of rosuvastatin is the sodium salt of rosuvastatin. In a preferred embodiment the pharmaceutically acceptable salts of pitavastatin are the potassium, sodium and the hemi-calcium salt of pitavastatin. A particularly preferred pharmaceutically acceptable salt of pitavastatin is the hemi-calcium salt of pitavastatin.

In a preferred embodiment, the above-mentioned fixed combination, non-fixed combination or kit of parts comprise a compound of the invention (in particular the compound of the invention is one of the examples of the invention), a lung surfactant and at least one pharmaceutically acceptable auxiliary. In a particularly preferred embodiment, the above-mentioned fixed combination, non-fixed combination or kit of parts comprise:
a compound of the invention and lusupultide,
a compound of the invention and poracant alfa,
a compound of the invention and sinapultide,
a compound of the invention and beracant,
a compound of the invention and bovacant,
a compound of the invention and colfosceril palmitate,
a compound of the invention and surfactant-TA, or
a compound of the invention and calfacant,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), an antibiotic and at least one pharmaceutically acceptable auxiliary. In a particularly preferred embodiment, the above-mentioned fixed combination, non-fixed combination or kit of parts comprise:
a compound of the invention and amoxicillin,
a compound of the invention and ampicillin,
a compound of the invention and levofloxacin,
a compound of the invention and clarithromycin,
a compound of the invention and ciprofloxacin,
a compound of the invention and telithromycin, or
a compound of the invention and azithromycin,
and at least one pharmaceutically acceptable auxiliary.

In a preferred embodiment, amoxicillin is used in form of its trihydrate. In another preferred embodiment, ampicillin is used in form of its trihydrate. In another preferred embodiment, the pharmaceutitally acceptable salt of ampicillin is ampicillin natrium. In another preferred embodiment levofloxacin is used in form of its hemi hydrate. In another preferred embodiment, the pharmaceutically acceptable salt of ciprofloxacin is ciprofloxacin hydrochloride monohydrate. In another preferred embodiment, azithromycin is used in form of its monohydrate.

In a preferred embodiment, the above-mentioned fixed combination, non-fixed combination or kit of parts comprise a compound of the invention (in particular the compound of the invention is one of the examples of the invention), a corticosteroid, a $\beta_2$-adrenoceptor agonist and at least one pharmaceutically acceptable auxiliary. In a particularly preferred embodiment, the above-mentioned fixed combination, non-fixed combination or kit of parts comprise:
a compound of the invention, budesonide and salbutamol,
a compound of the invention, budesonide and milveterol,
a compound of the invention, budesonide and indacaterol,
a compound of the invention, budesonide and carmoterol,
a compound of the invention, budesonide and salmeterol,
a compound of the invention, budesonide and formoterol,
a compound of the invention, fluticasone and salbutamol,
a compound of the invention, fluticasone and milveterol,
a compound of the invention, fluticasone and indacaterol,
a compound of the invention, fluticasone and carmoterol,
a compound of the invention, fluticasone and salmeterol,
a compound of the invention, fluticasone and formoterol,
a compound of the invention, beclometasone and salbutamol,
a compound of the invention, beclometasone and milveterol,
a compound of the invention, beclometasone and indacaterol,
a compound of the invention, beclometasone and carmoterol,
a compound of the invention, beclometasone and salmeterol,
a compound of the invention, beclometasone and formoterol,
a compound of the invention, mometasone and salbutamol,
a compound of the invention, mometasone and milveterol,
a compound of the invention, mometasone and indacaterol,
a compound of the invention, mometasone and carmoterol,
a compound of the invention, mometasone and salmeterol,
a compound of the invention, mometasone and formoterol,
a compound of the invention, triamcinolone acetonide and salbutamol,
a compound of the invention, triamcinolone acetonide and milveterol,
a compound of the invention, triamcinolone acetonide and indacaterol,
a compound of the invention, triamcinolone acetonide and carmoterol,
a compound of the invention, triamcinolone acetonide and salmeterol,
a compound of the invention, triamcinolone acetonide and formoterol,
a compound of the invention, ciclesonide and salbutamol,
a compound of the invention, ciclesonide and milveterol,
a compound of the invention, ciclesonide and indacaterol,
a compound of the invention, ciclesonide and carmoterol,
a compound of the invention, ciclesonide and salmeterol, or
a compound of the invention, ciclesonide and formoterol,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a $\beta_2$-adrenoceptor agonist, an anticholinergic and at least one pharmaceutically acceptable auxiliary. In a particularly preferred embodiment, the above-mentioned fixed combination, non-fixed combination or kit of parts comprise:

a compound of the invention, salbutamol and glycopyrronium bromide,
a compound of the invention, salbutamol and aclidinium bromide,
a compound of the invention, salbutamol and tiotropium bromide,
a compound of the invention, salbutamol and ipratropium bromide,
a compound of the invention, milveterol and glycopyrronium bromide,
a compound of the invention, milveterol and aclidinium bromide,
a compound of the invention, milveterol and tiotropium bromide,
a compound of the invention, milveterol and ipratropium bromide,
a compound of the invention, salmeterol and glycopyrronium bromide,
a compound of the invention, salmeterol and aclidinium bromide,
a compound of the invention, salmeterol and tiotropium bromide,
a compound of the invention, salmeterol and ipratropium bromide,
a compound of the invention, formoterol and glycopyrronium bromide,
a compound of the invention, formoterol and aclidinium bromide,
a compound of the invention, formoterol and tiotropium bromide,
a compound of the invention, formoterol and ipratropium bromide,
a compound of the invention, indacaterol and glycopyrronium bromide,
a compound of the invention, indacaterol and aclidinium bromide,
a compound of the invention, indacaterol and tiotropium bromide,
a compound of the invention, indacaterol and ipratropium bromide,
a compound of the invention, carmoterol and glycopyrronium bromide,
a compound of the invention, carmoterol and aclidinium bromide,
a compound of the invention, carmoterol and tiotropium bromide, or
a compound of the invention, carmoterol and ipratropium bromide,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a corticosteroid, an anticholinergic and at least one pharmaceutically acceptable auxiliary. In a particularly preferred embodiment, the above-mentioned fixed combination, non-fixed combination or kit of parts comprise:

a compound of the invention, budesonide and glycopyrronium bromide,
a compound of the invention, budesonide and aclidinium bromide,
a compound of the invention, budesonide and tiotropium bromide,
a compound of the invention, budesonide and ipratropium bromide,
a compound of the invention, fluticasone and glycopyrronium bromide,
a compound of the invention, fluticasone and aclidinium bromide,
a compound of the invention, fluticasone and tiotropium bromide,
a compound of the invention, fluticasone and ipratropium bromide,
a compound of the invention, beclometasone and glycopyrronium bromide,
a compound of the invention, beclometasone and aclidinium bromide,
a compound of the invention, beclometasone and tiotropium bromide,
a compound of the invention, beclometasone and ipratropium bromide,
a compound of the invention, mometasone and glycopyrronium bromide,
a compound of the invention, mometasone and aclidinium bromide,
a compound of the invention, mometasone and tiotropium bromide,
a compound of the invention, mometasone and ipratropium bromide,
a compound of the invention, triamcinolone acetonide and glycopyrronium bromide,
a compound of the invention, triamcinolone acetonide and aclidinium bromide,
a compound of the invention, triamcinolone acetonide and tiotropium bromide,
a compound of the invention, triamcinolone acetonide and ipratropium bromide,
a compound of the invention, ciclesonide and glycopyrronium bromide,
a compound of the invention, ciclesonide and aclidinium bromide,
a compound of the invention, ciclesonide and tiotropium bromide, or
a compound of the invention, ciclesonide and ipratropium bromide,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), an anti-diabetic agent and at least one pharmaceutically acceptable auxiliary. In a particularly preferred embodiment, the above-mentioned fixed combination, non-fixed combination or kit of parts comprise:

a compound of the invention and metformin,
a compound of the invention and carbutamide,
a compound of the invention and tolbutamide,
a compound of the invention and glibornuride,
a compound of the invention and glibenclamide,
a compound of the invention and glimepiride,
a compound of the invention and gliquidone,
a compound of the invention and glisoxepide,
a compound of the invention and repaglinide,
a compound of the invention and rosiglitazone,
a compound of the invention and pioglitazone,
a compound of the invention and rivoglitazone, a compound of the invention and exenatide,
a compound of the invention and albiglutide,
a compound of the invention and liraglutide,
a compound of the invention and sitagliptin,
a compound of the invention and saxagliptin,
a compound of the invention and vildagliptin, or
a compound of the invention and denagliptin,
and at least one pharmaceutically acceptable auxiliary.

In a preferred embodiment the pharmaceutically acceptable salt of metformin is the hydrochloride salt of metformin. In another preferred embodiment the pharmaceutically acceptable salt of tolbutamide is the sodium salt of tolbutamide. In another preferred embodiment the pharmaceutically acceptable salt of gliquidone is the sodium salt of gliquidone. In another preferred embodiment the pharmaceutically acceptable salt of rosiglitazone is the maleate salt of rosiglitazone. In another preferred embodiment the pharmaceutically acceptable salt of pioglitazone is the dihydrochloride salt of pioglitazone. In another preferred embodiment the pharmaceutically acceptable salt of rivoglitazone is the hydrochloride salt of rivoglitazone. In another preferred embodiment the pharmaceutically acceptable salt of sitagliptin is the phosphate salt of sitagliptin.

The pharmaceutical compositions according to the invention preferably contain the compound or compounds of the invention in a total amount of from 0.1 to 99.9 wt %, more preferably 5 to 95 wt %, in particular 20 to 80 wt %. In case of co-administration of at least one compound of the invention with at least one therapeutic agent selected from the group consisting of corticosteroids, anticholinergics, $\beta_2$-adrenoceptor agonists, H1 receptor antagonists, leukotriene receptor antagonists, type 5 phosphodiesterase inhibitors, HMG-CoA reductase inhibitors, lung surfactants, antibiotics and anti-diabetic agents, in form of a fixed combination, non-fixed combination or kit of parts the total amount of the compound(s) of the invention and said therapeutic agent(s) in the respective pharmaceutical compositions/formulations is preferably in the range of from 0.1 to 99.9 wt %, more preferably 5 to 95 wt %, in particular 20 to 80 wt %, under the provision that the total amount of the compound(s) of the invention and the therapeutic agent(s) does not exceed 100 wt %. Preferably, the at least one compound of the invention and the at least one therapeutic agent are present in the pharmaceutical compositions/formulations in a weight ratio of from 1000:1 to 1:1000.

As pharmaceutically acceptable auxiliaries, any auxiliaries known to be suitable for preparing pharmaceutical compositions/formulations can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions/formulations can be formulated, for example, into tablets, coated tablets (dragees), pills, cachets, capsules (caplets), granules, powders, suppositories, solutions (e.g., but not limited to, sterile solutions), emulsions, suspensions, ointments, creams, lotions, pastes, oils, gels, sprays and patches (e.g., but not limited to, transdermal therapeutic systems). Additionally, the pharmaceutical compositions can be prepared as e.g. liposome delivery systems, systems in which the compound of the invention is coupled to monoclonal antibodies and systems in which the compound of the invention is coupled to polymers (e.g., but not limited to, soluble or biodegradable polymers).

The pharmaceutical compositionsfformulations can be manufactured in a manner known to a person skilled in the art, e.g. by dissolving, mixing, granulating, dragee-making, levigating, emulsifying, encapsulating, entrapping or lyophilizing processes.

The selected formulation depends inter alia on the route of administering the pharmaceutical composition. The pharmaceutical compositions/formulations of the invention can be administered by any suitable route, for example, by the oral, sublingual, buccal, intravenous, intraarterial, intramuscular, subcutaneous, intracutaneous, topical, transdermal, intranasal, intraocular, intraperitoneal, intrasternal, intracoronary, transurethral, rectal or vaginal route, by inhalation or by insufflation. Oral administration of the compounds of the invention is preferred.

In case of non-fixed combinations or kit of parts comprising at least one of the compounds of the invention and at least one therapeutic agent selected from the group consisting of corticosteroids, anticholinergics, $\beta_2$-adrenoceptor agonists, H1 receptor antagonists, leukotriene receptor antagonists, type 5 phosphodiesterase inhibitors, HMG-CoA reductase inhibitors, lung surfactants, antibiotics and anti-diabetic agents, the compound of the invention and the therapeutic agent may be administered by the same route, e.g., without limitation, orally, or by different routes, e.g., without limitation, the compound of the invention can be administered orally and the therapeutic agent can be administered by inhalation or instillation.

Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the compound of the invention to a biodegradable polymer.

Administration by inhalation or instillation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of the compound of the invention to be administered, the aerosol-producing device can contain the compound in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (cosolvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 μm, more preferably it is in the range of from 0.5 to 10 µm, in particular in the range of from 2 to 6 µm (D50 value, measured by laser diffraction).

Specific aerosol-producing devices which may be used for inhaled administration include, but are not limited to, Cyclohaler®, Diskhaler®, Rotadisk®, Turbohaler®, Autohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

In case of topical administration, suitable pharmaceutical formulations are, for example, ointments, creams, lotions, pastes, gels, powders, solutions, emulsions, suspensions, oils, sprays and patches (e.g., but not limited to, transdermal therapeutic systems).

For parenteral modes of administration such as, for example, intravenous, intraarterial, intramuscular, subcutaneous, intracutaneous, intraperitoneal and intrasternal administration, preferably solutions (e.g., but not limited to, sterile solutions, isotonic solutions) are used. They are preferably administered by injection or infusion techniques.

In case of intranasal administration, for example, sprays and solutions to be applied in drop form are preferred formulations.

For intraocular administration, solutions to be applied in drop form, gels and ointments are exemplified formulations.

Generally, the pharmaceutical compositions according to the invention can be administered such that the dose of the compound of the invention is in the range customary for type 4 phosphodiesterase inhibitors. In particular, a dose in the range of from 0.01 to 250 mg, preferably in the range of 0.05 to 100 mg, more preferably in the range of 0.05 to 10 mg of the compound of the invention per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

In case of co-administration of at least one compound of the invention with at least one therapeutic agent selected from the group consisting of corticosteroids, anticholinergics, (β$_2$-adrenoceptor agonists, H1 receptor antagonists, leukotriene receptor antagonists, type 5 phosphodiesterase inhibitors, HMG-CoA reductase inhibitors, lung surfactants, antibiotics and anti-diabetic agents, in form of a fixed combination, non-fixed combination or kit of parts the dose of the compound of the invention as well as the dose of the therapeutic agent will be in a range customary for the mono-therapy, it more likely being possible, on account of the individual action, which are mutually positively influencing and reinforcing, to reduce the respective doses in case of co-administration of the compound(s) of the invention and the therapeutic agent.

The pharmaceutical compositions of the invention can be administered in a single dose per day or in multiple subdoses, for example, 2 to 4 doses per day. A single dose unit of the pharmaceutical composition can contain e.g. from 0.01 mg to 250 mg, preferably 0.05 mg to 100 mg, more preferably 0.05 to 10 mg of the compound of the invention.

In case of co-administration of at least one compound of the invention and at least one therapeutic compound selected from the group consisting of corticosteroids, anticholinergics, β$_2$-adrenoceptor agonists, H1 receptor antagonists, leukotriene receptor antagonists, type 5 phosphodiesterase inhibitors, HMG-CoA reductase inhibitors, lung surfactants, antibiotics and anti-diabetic agents, in form of a fixed combination, a non-fixed combination or a kit of parts a single dose unit of the respective Pharmaceutical composition/formulation can contain e.g. from 0.01 mg to 250 mg, preferably 0.05 mg to 100 mg, more preferably 0.05 to 10 mg of the compound of the invention and/or e.g. from 0.01 mg to 4000 mg, preferably 0.1 mg to 2000 mg, more preferably 0.5 mg to 1000 mg, most preferably 1 mg to 500 mg, of the therapeutic agent.

Furthermore, the pharmaceutical composition/formulation can be adapted to weekly, monthly or even more infrequent administration, for example by using an implant, e.g. a subcutaneous or intramuscular implant, by using the compound of the invention in form of a sparingly soluble salt or by using the compound of the invention coupled to a polymer. Administration of the pharmaceutical composition/formulation in a single dose per day is preferred.

Biological Investigations

The second messenger cyclic AMP (cAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21-40, "The Handbook of Immunopharmacology", Academic Press, 1996), and its inhibition leads to an increase of the intracellular cAMP concentration and thus to the inhibition of cellular activation (JE Souness et al., Immunopharmacology 47: 127-162, 2000).

The antiinflammatory potential of PDE4 inhibitors in vivo in various animal models has been described (MM Teixeira, TiPS 18: 164-170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor-a in monocytes, macrophages or dendritic cells (Gantner et al., Brit J Pharmacol 121: 221-231, 1997, and Pulmonary Pharmacol Therap 12: 377-386, 1999). In addition, the immunomodulatory potential of PDE4 inhibitors is evident from the inhibition of T-cell responses like cytokine synthesis or proliferation (DM Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Method for Measuring Inhibition of PDE4 Activity

The PDE4B1 (GB no. L20966) was a gift of Prof. M. Conti (Stanford University, USA). It was amplified from the original plasmid (pCMV5) via PCR with primers Rb18 (5'-CAGACATCCTAAGAGGGGAT-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmids were cotransfected with Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times. PDE4B1 was expressed in SF21 cells by infecting $2 \times 10^6$ cells/ml with an MOI (multiplicity of infection) between 1 and 10 in the serum-free medium Insect Express Sf9-S2

(PAA, Pasching, Austria). The cells were cultured at 28° C. for 48-72 hours, after which they were pelleted for 5-10 min at 1000×g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM β-mercaptoethanol, 2 mM benzamidine, 0.4 mM Pefablock, 10 µM leupeptin, 10 µM pepstatin A, 5 µM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE4B1 activity was inhibited by the compounds according to the invention in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 µl and contains 20 mM Tris buffer (pH 7.4), 0.1 mg/ml of BSA, 5 mM $Mg^{2+}$, 0.5 µM cAMP (including about 50,000 cpm of [3H]cAMP), 1 µl of the respective substance dilution in DMSO and sufficient recombinant PDE (1000×g supernatant, see above) to ensure that 10-20% of the cAMP is converted under the said experimental conditions. The final concentration of DMSO in the assays (1% v/v) does not substantially affect the activity of the PDE investigated. After a preincubation of 5 min at 37° C., the reaction is started by adding the substrate (cAMP) and the assays are incubated for a further 15 min; after that, they are stopped by adding SPA beads (50 µl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE4B1 activity are determined from the concentration-effect curves by means of non-linear regression.

The inhibitory values determined for the compounds according to the invention follow from the following Table 1, in which the numbers of the compounds correspond to the numbers of the examples.

TABLE 1

Inhibition of PDE4 acitivity [measured as −log$IC_{50}$ (mol/l)]

| Compound | PDE4 Inhibition |
|---|---|
| 1 | 8.29 |
| 2 | 8.09 |
| 3 | 7.75 |
| 4 | 7.74 |
| 5 | 7.15 |
| 6 | 6.84 |
| 7 | 7.65 |
| 8 | 8.53 |
| 9 | 8.23 |
| 11 | 8.08 |
| 12 | 7.46 |
| 13 | 7.79 |
| 14 | 9.06 |
| 15 | 7.90 |
| 16 | 7.48 |
| 17 | 8.27 |
| 18 | 8.42 |
| 19 | 7.48 |
| 20 | 8.24 |

The invention claimed is:
1. A compound of formula 1

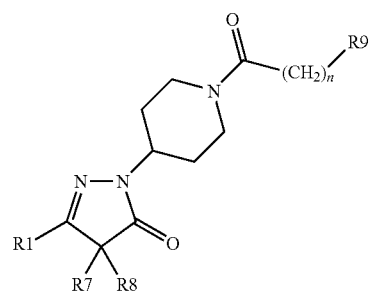

wherein
R1 represents a phenyl derivative of formulae (a) or (b)

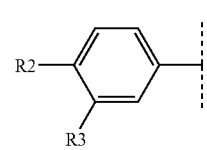

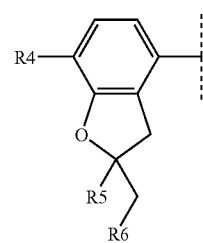

wherein
R2 is selected from the group consisting of 1-2C-alkoxy and 1-2C-alkoxy which is completely or predominantly substituted by fluorine;
R3 is selected from the group consisting of 1-2C-alkoxy, 3-5C-cycloalkoxy, 3-5C-cycloalkylmethoxy and 1-2C-alkoxy which is completely or predominantly substituted by fluorine;
R4 is selected from the group consisting of 1-2C-alkoxy and 1-2C-alkoxy which is completely or predominantly substituted by fluorine;
R5 is 1-2C-alkyl;
R6 is selected from the group consisting of hydrogen and 1-2C-alkyl;
or R5 and R6 together and with inclusion of the two carbon atoms, to which they are bonded, form a spiro-linked 5- or 6-membered hydrocarbon ring;
R7 is 1-3C-alkyl;
R8 is 1-3C-alkyl;
or R7 and R8 together with the carbon atom, to which they are bonded, form a spiro-linked 3-, 4-, 5- or 6-membered hydrocarbon ring;
R9 is —N(R11)R12,
wherein
R11 and R12 together and with inclusion of the nitrogen atom to which they are bonded, form a heterocyclic ring selected from the group consisting of a pyrrolidin-2,5-dione-1-yl-, isoindol-1,3-dione-2-yl-, 2-oxo-2,3-dihydro-1H-indol-1-yl-, pyrrolidin-2-one-1-yl-, piperidin-2,6-dione-1-yl-, morpholin-3,5-dione-4-yl-, thiomorpholin-3,5-dione-4-yl-, thiomorpholine-1-oxide-3,5-dione-4-yl- and a thiomorpholine-1,1-dioxide-3,5-dione-4-yl-ring; and n is 1 or 2;

or a stereoisomer thereof.

2. A compound of formula 1 according to claim 1, wherein R1 represents a phenyl derivative of formulae (a) or (b)

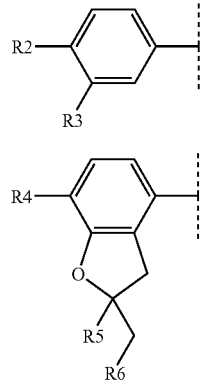

wherein
  R2 is selected from the group consisting of 1-2C-alkoxy and 1-2C-alkoxy which is completely or predominantly substituted by fluorine;
  R3 is selected from the group consisting of 1-2C-alkoxy, 3-5C-cycloalkoxy, 3-5C-cycloalkylmethoxy and 1-2C-alkoxy which is completely or predominantly substituted by fluorine;
  R4 is selected from the group consisting of 1-2C-alkoxy and 1-2C-alkoxy which is completely or predominantly substituted by fluorine;
  R5 is 1-2C-alkyl;
  R6 is selected from the group consisting of hydrogen and 1-2C-alkyl;
  or R5 and R6 together and with inclusion of the two carbon atoms, to which they are bonded, form a spiro-linked 5- or 6-membered hydrocarbon ring;
  R7 is 1-3C-alkyl;
  R8 is 1-3C-alkyl;
or R7 and R8 together with the carbon atom, to which they are bonded, form a spiro-linked 3-, 4-, 5- or 6-membered hydrocarbon ring;
  R9 is —N(R11)R12,
  wherein
    R11 and R12 together and with inclusion of the nitrogen atom to which they are bonded, form a heterocyclic ring selected from the group consisting of a pyrrolidin-2,5-dione-1-yl-, isoindol-1,3-dione-2-yl-, pyrrolidin-2-one-1-yl-, piperidin-2,6-dione-1-yl, morpholin-3,5-dione-4-yl-, thiomorpholin-3,5-dione-4-yl-, thiomorpholine-1-oxide-3,5-dione-4-yl- and thiomorpholine-1,1-dioxide-3,5-dione-4-yl-ring, and
  n is 1 or 2;
  or a stereoisomer thereof.

3. A compound of formula 1 according to claim 1, wherein R1 represents a phenyl derivative of formulae (a) or (b)

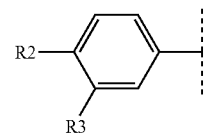

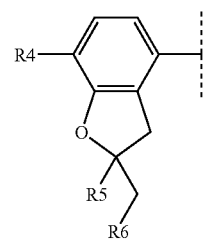

wherein
  R2 is selected from the group consisting of 1-2C-alkoxy and 1-2C-alkoxy which is completely or predominantly substituted by fluorine;
  R3 is selected from the group consisting of 1-2C-alkoxy and 1-2C-alkoxy which is completely or predominantly substituted by fluorine;
  R4 is selected from the group consisting of 1-2C-alkoxy and 1-2C-alkoxy which is completely or predominantly substituted by fluorine;
  R5 is 1-2C-alkyl;
  R6 is selected from the group consisting of hydrogen and 1-2C-alkyl;
  or R5 and R6 together and with inclusion of the two carbon atoms, to which they are bonded, form a spiro-linked 5- or 6-membered hydrocarbon ring;
  R7 is 1-3C-alkyl;
  R8 is 1-3C-alkyl;
  or R7 and R8 together with the carbon atom, to which they are bonded, form a spiro-linked 5- or 6-membered hydrocarbon ring;
  R9 is —N(R11)R12,
  wherein
    R11 and R12 together and with inclusion of the nitrogen atom to which they are bonded, form a heterocyclic ring selected from the group consisting of a pyrrolidin-2,5-dione-1-yl-, isoindol-1,3-dione-2-yl-, 2-oxo-2,3-dihydro-1H-indol-1-yl-, pyrrolidin-2-one-1-yl-, piperidin-2,6-dione-1-yl-, morpholin-3,5-dione-4-yl-, thiomorpholin-3,5-dione-4-yl-, thiomorpholine-1-oxide-3,5-dione-4-yl- and thiomorpholine-1,1-dioxide-3,5-dione-4-yl-ring; and
  n is 1 or 2;
  or a stereoisomer thereof.

4. A compound of formula 1 according to claim 1, wherein R1 represents a phenyl derivative of formulae (a) or (b)

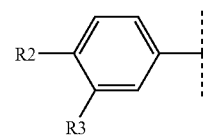

-continued

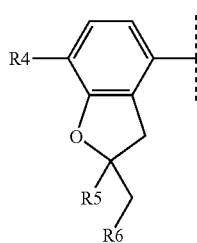
(b)

wherein
R2 is selected from the group consisting of 1-2C-alkoxy and 1-2C-alkoxy which is completely or predominantly substituted by fluorine;
R3 is selected from the group consisting of 1-2C-alkoxy and 1-2C-alkoxy which is completely or predominantly substituted by fluorine;
R4 is selected from the group consisting of 1-2C-alkoxy and 1-2C-alkoxy which is completely or predominantly substituted by fluorine;
R5 is 1-2C-alkyl;
R6 is selected from the group consisting of hydrogen and 1-2C-alkyl;
or R5 and R6 together and with inclusion of the two carbon atoms, to which they are bonded, form a spiro-linked 5- or 6-membered hydrocarbon ring;
R7 is 1-3C-alkyl;
R8 is 1-3C-alkyl;
or R7 and R8 together with the carbon atom, to which they are bonded, form a spiro-linked 5- or 6-membered hydrocarbon ring;
R9 is —N(R11)R12,
wherein
R11 and R12 together and with inclusion of the nitrogen atom to which they are bonded, form a heterocyclic ring selected from the group consisting of a pyrrolidin-2,5-dione-1-yl-, isoindol-1,3-dione-2-yl-, pyrrolidin-2-one-1-yl, piperidin-2,6-dione-1-yl, morpholin-3,5-dione-4-yl-, thiomorpholin-3,5-dione-4-yl-, thiomorpholine-1-oxide-3,5-dione-4-yl- and thiomorpholine-1,1-dioxide-3,5-dione-4-yl-ring; and
n is 1 or 2;
or a stereoisomer thereof.

5. A compound of formula 1 according to claim 1, wherein R1 represents a phenyl derivative of formulae (a) or (b)

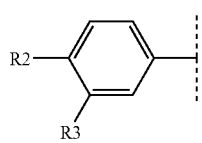
(a)

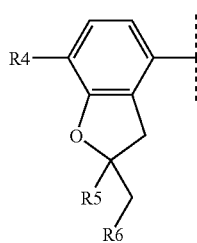
(b)

wherein
R2 is selected from the group consisting of 1-2C-alkoxy and 1-2C-alkoxy which is completely or predominantly substituted by fluorine;
R3 is selected from the group consisting of 1-2C-alkoxy and 1-2C-alkoxy which is completely or predominantly substituted by fluorine;
R4 is selected from the group consisting of 1-2C-alkoxy and 1-2C-alkoxy which is completely or predominantly substituted by fluorine;
R5 is methyl;
R6 is hydrogen;
or R5 and R6 together and with inclusion of the two carbon atoms, to which they are bonded, form a spiro-linked 5- or 6-membered hydrocarbon ring;
R7 is 1-3C-alkyl;
R8 is 1-3C-alkyl;
R9 is —N(R11)R12,
wherein
R11 and R12 together and with inclusion of the nitrogen atom to which they are bonded, form a heterocyclic ring selected from the group consisting of a pyrrolidin-2,5-dione-1-yl-, morpholin-3,5-dione-4-yl-, thiomorpholin-3,5-dione-4-yl- and thiomorpholine-1,1-dioxide-3,5-dione-4-yl-ring; and
n is 1 or 2;
or a stereoisomer thereof.

6. A compound of formula 1 according to claim 1, wherein R1 represents a phenyl derivative of formulae (a) or (b)

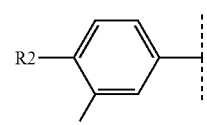
(a)

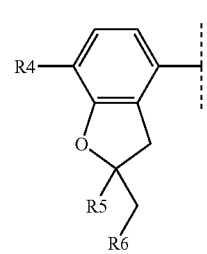
(b)

wherein
R2 is methoxy;
R3 is methoxy;
R4 is methoxy;
R5 is methyl;
R6 is hydrogen;
or R5 and R6 together and with inclusion of the two carbon atoms, to which they are bonded, form a spiro-linked 5- or 6-membered hydrocarbon ring;
R7 is methyl;
R8 is methyl;
R9 is —N(R11)R12,
wherein
R11 and R12 together and with inclusion of the nitrogen atom to which they are bonded, form a heterocyclic ring selected from the group consisting of a pyrrolidin-2,5-dione-1-yl-, morpholin-3,5-dione-4-yl- and a thiomorpholin-3,5-dione-4-yl-ring, and
n is 1.

7. A compound according to claim 1 selected from the group consisting of 4-(2-{4-[3-(3,4-dimethoxyphenyl)-4,4-dimethyl-5-oxo-4,5-dihydro-1H-pyrazol-1-yl]piperidin-1-yl}-2-oxoethyl)morpholine-3,5-dione;
1-(2-{4-[3-(3,4-dimethoxyphenyl)-4,4-dimethyl-5-oxo-4,5-dihydro-1H-pyrazol-1-yl]piperidin-1-yl}-2-oxoethyl)pyrrolidine-2,5-dione;
1-(2-{4-[3-(3,4-diethoxyphenyl)-4,4-dimethyl-5-oxo-4,5-dihydro-1H-pyrazol-1-yl]piperidin-1-yl}-2-oxoethyl)pyrrolidine-2,5-dione;
1-[2-(4-{3-[3-(cyclopropylmethoxy)-4-(difluoromethoxy)phenyl]-4,4-dimethyl-5-oxo-4,5-dihydro-1H-pyrazol-1-yl}piperidin-1-yl)-2-oxoethyl]pyrrolidine-2,5-dione;
1-[2-(4-{3-[3-(cyclopropylmethoxy)-4-methoxyphenyl]-4,4-dimethyl-5-oxo-4,5-dihydro-1H-pyrazol-1-yl}piperidin-1-yl)-2-oxoethyl]pyrrolidine-2,5-dione;
1-[2-(4-{3-[4-methoxy-3-(2,2,2-trifluoroethoxy)phenyl]-4,4-dimethyl-5-oxo-4,5-dihydro-1H-pyrazol-1-yl}piperidin-1-yl)-2-oxoethyl]pyrrolidine-2,5-dione;
1-(2-{4-[3-(3-ethoxy-4-methoxyphenyl)-4,4-dimethyl-5-oxo-4,5-dihydro-1H-pyrazol-1-yl]piperidin-1-yl}-2-oxoethyl)pyrrolidine-2,5-dione;
1-(2-{4-[3-(7-methoxy-2,2-dimethyl-2,3-dihydro-1-benzofuran-4-yl)-4,4-dimethyl-5-oxo-4,5-dihydro-1H-pyrazol-1-yl]piperidin-1-yl}-2-oxoethyl)pyrrolidine-2,5-dione;
1-(2-{4-[3-(7-methoxy-3H-spiro[1-benzofuran-2,1'-cyclopentan]-4-yl)-4,4-dimethyl-5-oxo-4,5-dihydro-1H-pyrazol-1-yl]piperidin-1-yl}-2-oxoethyl)pyrrolidine-2,5-dione;
1-(2-{4-[3-(3,4-dimethoxyphenyl)-4,4-diethyl-5-oxo-4,5-dihydro-1H-pyrazol-1-yl]piperidin-1-yl}-2-oxoethyl)pyrrolidine-2,5-dione;
1-(2-{4-[3-(3,4-dimethoxyphenyl)-4-methyl-5-oxo-4-propyl-4,5-dihydro-1H-pyrazol-1-yl]piperidin-1-yl}-2-oxoethyl)pyrrolidine-2,5-dione;
1-(2-{4-[3-(3,4-dimethoxyphenyl)-4-ethyl-4-methyl-5-oxo-4,5-dihydro-1H-pyrazol-1-yl]piperidin-1-yl}-2-oxoethyl)pyrrolidine-2,5-dione;
1-(2-{4-[4-(3,4-dimethoxyphenyl)-1-oxo-2,3-diazaspiro[4.4]non-3-en-2-yl]piperidin-1-yl}-2-oxoethyl)pyrrolidine-2,5-dione;
2-(2-{4-[3-(3,4-dimethoxyphenyl)-4,4-dimethyl-5-oxo-4,5-dihydro-1H-pyrazol-1-yl]piperidin-1-yl}-2-oxoethyl)-1H-isoindole-1,3(2H)-dione;
5-(3,4-dimethoxyphenyl)-4,4-dimethyl-2-{1-[(2-oxopyrrolidin-1-yl)acetyl]piperidin-4-yl}-2,4-dihydro-3H-pyrazol-3-one;
1-(2-{4-[3-(3,4-Dimethoxy-phenyl)-4,4-dimethyl-5-oxo-4,5-dihydro-pyrazol-1-yl]-piperidin-1-yl}-2-oxo-ethyl)-piperidine-2,6-dione;
4-(2-{4-[3-(3,4-dimethoxyphenyl)-4,4-dimethyl-5-oxo-4,5-dihydro-1H-pyrazol-1-yl]piperidin-1-yl}-2-oxoethyl)thiomorpholine-3,5-dione;
4-(2-{4-[3-(3,4-dimethoxyphenyl)-4,4-dimethyl-5-oxo-4,5-dihydro-1H-pyrazol-1-yl]piperidin-1-yl}-2-oxoethyl)thiomorpholine-3,5-dione 1,1-dioxide;
1-(3-{4-[3-(3,4-Dimethoxy-phenyl)-4,4-dimethyl-5-oxo-4,5-dihydro-pyrazol-1-yl]-piperidin-1-yl}-3-oxo-propyl)-pyrrolidine-2,5-dione;

and stereoisomers thereof.

8. A compound according to claim 1 selected from the group consisting of 4-(2-{4-[3-(3,4-dimethoxyphenyl)-4,4-dimethyl-5-oxo-4,5-dihydro-1H-pyrazol-1-yl]piperidin-1-yl}-2-oxoethyl)morpholine-3,5-dione;
1-(2-{4-[3-(3,4-dimethoxyphenyl)-4,4-dimethyl-5-oxo-4,5-dihydro-1H-pyrazol-1-yl]piperidin-1-yl}-2-oxoethyl)pyrrolidine-2,5-dione;
1-(2-{4-[3-(3,4-diethoxyphenyl)-4,4-dimethyl-5-oxo-4,5-dihydro-1H-pyrazol-1-yl]piperidin-1-yl}-2-oxoethyl)pyrrolidine-2,5-dione;
1-[2-(4-{3-[3-(cyclopropylmethoxy)-4-(difluoromethoxy)phenyl]-4,4-dimethyl-5-oxo-4,5-dihydro-1H-pyrazol-1-yl}piperidin-1-yl)-2-oxoethyl]pyrrolidine-2,5-dione;
1-[2-(4-{3-[3-(cyclopropylmethoxy)-4-methoxyphenyl]-4,4-dimethyl-5-oxo-4,5-dihydro-1H-pyrazol-1-yl}piperidin-1-yl)-2-oxoethyl]pyrrolidine-2,5-dione;
1-[2-(4-{3-[4-methoxy-3-(2,2,2-trifluoroethoxy)phenyl]-4,4-dimethyl-5-oxo-4,5-dihydro-1H-pyrazol-1-yl}piperidin-1-yl)-2-oxoethyl]pyrrolidine-2,5-dione;
1-(2-{4-[3-(3-ethoxy-4-methoxyphenyl)-4,4-dimethyl-5-oxo-4,5-dihydro-1H-pyrazol-1-yl]piperidin-1-yl}-2-oxoethyl)pyrrolidine-2,5-dione,
1-(2-{4-[3-(7-methoxy-2,2-dimethyl-2,3-dihydro-1-benzofuran-4-yl)-4,4-dimethyl-5-oxo-4,5-dihydro-1H-pyrazol-1-yl]piperidin-1-yl}-2-oxoethyl)pyrrolidine-2,5-dione;
1-(2-{4-[3-(7-methoxy-3H-spiro[1-benzofuran-2,1'-cyclopentan]-4-yl)-4,4-dimethyl-5-oxo-4,5-dihydro-1H-pyrazol-1-yl]piperidin-1-yl}-2-oxoethyl)pyrrolidine-2,5-dione;
1-(2-{4-[3-(3,4-dimethoxyphenyl)-4,4-diethyl-5-oxo-4,5-dihydro-1H-pyrazol-1-yl]piperidin-1-yl}-2-oxoethyl)pyrrolidine-2,5-dione;
1-(2-{4-[3-(3,4-dimethoxyphenyl)-4-methyl-5-oxo-4-propyl-4,5-dihydro-1H-pyrazol-1-yl]piperidin-1-yl}-2-oxoethyl)pyrrolidine-2,5-dione,
1-(2-{4-[3-(3,4-dimethoxyphenyl)-4-ethyl-4-methyl-5-oxo-4,5-dihydro-1H-pyrazol-1-yl]piperidin-1-yl}-2-oxoethyl)pyrrolidine-2,5-dione;
1-(2-{4-[4-(3,4-dimethoxyphenyl)-1-oxo-2,3-diazaspiro[4.4]non-3-en-2-yl]piperidin-1-yl}-2-oxoethyl)pyrrolidine-2,5-dione;
2-(2-{4-[3-(3,4-dimethoxyphenyl)-4,4-dimethyl-5-oxo-4,5-dihydro-1H-pyrazol-1-yl]piperidin-1-yl}-2-oxoethyl)-1H-isoindole-1,3(2H)-dione;
5-(3,4-dimethoxyphenyl)-4,4-dimethyl-2-{1-[(2-oxopyrrolidin-1-yl)acetyl]piperidin-4-yl}-2,4-dihydro-3H-pyrazol-3-one;
1-(2-{4-[3-(3,4-Dimethoxy-phenyl)-4,4-dimethyl-5-oxo-4,5-dihydro-pyrazol-1-yl]-piperidin-1-yl}-2-oxoethyl)-piperidine-2,6-dione;
4-(2-{4-[3-(3,4-dimethoxyphenyl)-4,4-dimethyl-5-oxo-4,5-dihydro-1H-pyrazol-1-yl]piperidin-1-yl}-2-oxoethyl)thiomorpholine-3,5-dione;
4-(2-{4-[3-(3,4-dimethoxyphenyl)-4,4-dimethyl-5-oxo-4,5-dihydro-1H-pyrazol-1-yl]piperidin-1-yl}-2-oxoethyl)thiomorpholine-3,5-dione 1,1-dioxide;
1-(3-{4-[3-(3,4-Dimethoxy-phenyl)-4,4-dimethyl-5-oxo-4,5-dihydro-pyrazol-1-yl]-piperidin-1-yl}-3-oxo-propyl)-pyrrolidine-2,5-dione;
1-(2-{4-[3-(3,4-Dimethoxy-phenyl)-4,4-dimethyl-5-oxo-4,5-dihydro-pyrazol-1-yl]-piperidin-1-yl}-2-oxoethyl)-1,3-dihydro-2H-indol-2-one;

and stereoisomers thereof.

9. A pharmaceutical composition comprising at least one of the compounds or stereoisomers of the compounds according to claim 1 together with at least one pharmaceutically acceptable auxiliary.

10. A compound of formula 4,

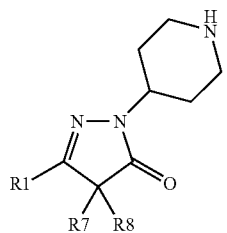

(4)

wherein
R1 represents a phenyl derivative of formulae (a) or (b)

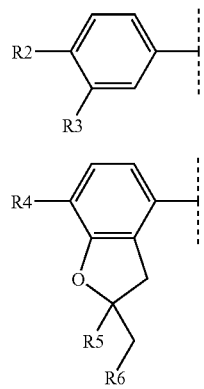

wherein
R2 is selected from the group consisting of 1-2C-alkoxy and 1-2C-alkoxy which is completely or predominantly substituted by fluorine;

R3 is selected from the group consisting of 1-2C-alkoxy, 3-5C-cycloalkoxy, 3-5C-cycloalkylmethoxy and 1-2C-alkoxy which is completely or predominantly substituted by fluorine;

R4 is selected from the group consisting of 1-2C-alkoxy and 1-2C-alkoxy which is completely or predominantly substituted by fluorine;

R5 is 1-2C-alkyl;

R6 is selected from the group consisting of hydrogen and 1-2C-alkyl;

or R5 and R6 together and with inclusion of the two carbon atoms, to which they are bonded, form a spiro-linked 5- or 6-membered hydrocarbon ring;

R7 is 1-3C-alkyl;

R8 is 1-3C-alkyl;

or R7 and R8 together with the carbon atom, to which they are bonded, form a spiro-linked 3-, 4-, 5- or 6-membered hydrocarbon ring;

a salt thereof, a stereoisomer thereof or a salt of the stereoisomer thereof.

11. A fixed combination comprising at least one of the compounds or stereoisomers of the compounds according to claim 1, at least one therapeutic agent selected from the group consisting of corticosteroids, anticholinergics, $\beta_2$-adrenoceptor agonists, H1 receptor antagonists, leukotriene receptor antagonists, type 5 phosphodiesterase inhibitors, HMG-CoA reductase inhibitors, lung surfactants and antibiotics, and at least one pharmaceutically acceptable auxiliary.

12. A fixed combination, non-fixed combination or kit of parts comprising at least one of the compounds or stereoisomers of the compounds according to claim 1, at least one therapeutic agent selected from the group consisting of corticosteroids, anticholinergics, $\beta_2$-adrenoceptor agonists, H1 receptor antagonists, leukotriene receptor antagonists, type 5 phosphodiesterase inhibitors, HMG-CoA reductase inhibitors, lung surfactants, antibiotics and anti-diabetic agents, and at least one pharmaceutically acceptable auxiliary.

13. A method for inhibiting type 4 phosphodiesterase in a patient comprising administering to a patient in need thereof a compound according to claim 1 or a stereoisomer thereof.

* * * * *